(12) United States Patent
Kim et al.

(10) Patent No.: US 10,822,367 B2
(45) Date of Patent: Nov. 3, 2020

(54) PHARMACEUTICAL COMPOSITION FOR PREVENTING OR TREATING DEMENTIA AND IMPROVING COGNITIVE FUNCTION, COMPRISING GLASSWORT EXTRACT

(71) Applicant: PHYTO CORPORATION INC., Seoul (KR)

(72) Inventors: Deuk-Hoi Kim, Goyang-si (KR); Mee-Hyang Kweon, Seoul (KR); Eun-Ah Cho, Seoul (KR); Joon Soo Kim, Chungju-si (KR); Hyun Joo Yoon, Suwon-si (KR); Seon Yeong Park, Seoul (KR)

(73) Assignee: PHYTO CORPORATION INC., Seoul (KR)

( * ) Notice: Subject to any disclaimer, the term of this patent is extended or adjusted under 35 U.S.C. 154(b) by 1 day.

(21) Appl. No.: 16/304,585

(22) PCT Filed: May 14, 2018

(86) PCT No.: PCT/KR2018/005502
§ 371 (c)(1),
(2) Date: Nov. 26, 2018

(87) PCT Pub. No.: WO2018/212531
PCT Pub. Date: Nov. 22, 2018

(65) Prior Publication Data
US 2019/0194241 A1    Jun. 27, 2019

(30) Foreign Application Priority Data
May 15, 2017  (KR) .......................... 10-2017-0059906

(51) Int. Cl.
| | |
|---|---|
| C07H 15/26 | (2006.01) |
| C07H 1/06 | (2006.01) |
| A61P 25/28 | (2006.01) |
| A23L 33/105 | (2016.01) |
| A61K 31/7034 | (2006.01) |
| A23K 20/121 | (2016.01) |
| A23L 33/10 | (2016.01) |
| A61K 36/21 | (2006.01) |
| A61K 31/34 | (2006.01) |

(52) U.S. Cl.
CPC ........... *C07H 15/26* (2013.01); *A23K 20/121* (2016.05); *A23L 33/10* (2016.08); *A23L 33/105* (2016.08); *A61K 31/34* (2013.01); *A61K 31/7034* (2013.01); *A61K 36/21* (2013.01); *A61P 25/28* (2018.01); *C07H 1/06* (2013.01)

(58) Field of Classification Search
CPC ........ A61P 20/28; A23L 33/10; A23L 33/105; A61K 36/21; A61K 31/7048; A61K 31/7034; A61K 31/34; C07H 1/06; C07H 15/26

USPC .......................................................... 514/25
See application file for complete search history.

(56) References Cited

U.S. PATENT DOCUMENTS

| | | | | |
|---|---|---|---|---|
| 4,816,481 | A | * | 3/1989 | Takasugi ................ A61K 31/34 514/25 |
| 2013/0310332 | A1 | | 11/2013 | Barbeau et al. |
| 2019/0142046 | A1 | | 5/2019 | Kim et al. |

FOREIGN PATENT DOCUMENTS

| | | |
|---|---|---|
| KR | 10-2005-0001556 A | 1/2005 |
| KR | 10-2010-0118921 A | 11/2010 |
| KR | 10-2015-0068803 A | 6/2015 |
| KR | 101691855 B1 | 1/2017 |
| KR | 10-2017-0126097 A | 11/2017 |

OTHER PUBLICATIONS

The Merck Manual, 1992, pp. 1403-1404 and 1493-1497.*
Karthivashan et al, Scientific Reports, 2018, 8:7174, pp. 1-16; published online May 8, 2018.*
International Search Report dated Sep. 20, 2018 for International Patent Application No. PCT/KR2018/005502, Kim et al., "Pharmaceutical Composition for Preventing or Treating Dementia and Improving Cognitive Function, Comprising Glasswort Extract," filed May 14, 2018 (7 pages).
Jang et al., "Antioxidant and antithrombus activities of enzyme-treated Salicornia herbacea extracts," Ann Nutr Metab. 51(2):119-25 (2007).

(Continued)

*Primary Examiner* — Ganapathy Krishnan
(74) *Attorney, Agent, or Firm* — Clark & Elbing LLP; Susan M. Michaud

(57) ABSTRACT

The present invention relates to a pharmaceutical composition comprising an acanthoside B compound as an effective ingredient for preventing or treating dementia or for improving a cognitive function. In the present invention, a desalted glasswort extract, and acanthoside B, which is isolated from the extract and acts as an effective ingredient inhibitory of acetylcholine esterase, were found to have an excellent neuroprotective activity through the inhibition of neuroinflammation and to improve memory retention and remarkably enhance spatial cognitive ability as measured by passive avoidance test and Y-maze test in a scopolamine-induced amnesic animal model. The acanthoside B or glasswort extract of the present invention can be applied to a pharmaceutical composition for preventing or treating dementia, a pharmaceutical composition for improving a cognitive function, or a health functional food or feed for improving memory retention and cognitive function.

3 Claims, 21 Drawing Sheets
Specification includes a Sequence Listing.

(56) References Cited

OTHER PUBLICATIONS

Karthivashan et al., "Ameliorative potential of desalted *Salicornia europaea* L. extract in multifaceted Alzheimer's-like scopolamine-induced amnesic mice model," Sci Rep. 8(1):7174 (16 pages), 2018.

Kim et al., "Neuroprotective effect of halophyte *Salicornia herbacea* L. is mediated by activation of heme oxygenase-1 in mouse hippocampal HT22 cells," J Med Food. 20(2):140-51 (2017).

Office Action dated Jun. 3, 2019 for Korean Patent Application No. 10-2019-0002451, Kim et al., "Food or Feed Composition for Improving Cognitive Function or Memory Comprising Extract of desalted Salicornia europaea," filed Jan. 8, 2019 (5 pages).

Minsun, Kim, Thesis: "Neuroprotective and Cognition-Enhancing Effects of *Salicornia herbacea* L.," Master of Agriculture, School of Food Science and Biotechnology, Kyungpook National University, Jun. 2016 (65 pages).

Fan et al., "Iridoid Glycosides and Glycosidic Constituents from Eriophyton wallichii Benth," Phytochemistry 72(14-15):1927-32 (2011).

Extended European Search Report for European Application No. 18802179.4, dated Jan. 8, 2020 (7 pages).

\* cited by examiner (A)

(B)

Acanthoside B
Molecular formula: $C_{28}H_{36}O_{13}$
Molecular Weight: 580

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
tgaagaaaac cccttgtgct                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ttctgtgctg tcccagtgag                                              20

<210> SEQ ID NO 3
<211> LENGTH: 22
<212> TYPE: DNA
<213> ORGANISM: Artificial Sequence
```

```
<220> FEATURE:
<223> OTHER INFORMATION: Synthetic Construct

<400> SEQUENCE: 3
caagacagat cataagcgag ga                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ggcgcagttt atgttgtctg t                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
ccaccacgct cttctgtcta c                                               21

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
agggtctggg ccatagaact                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tgtgaaatgc caccttttga                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ggtcaaaggt ttggaagcag                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgatgcactt gcagaaaaca                                                 20
```

```
<210> SEQ ID NO 10
<211> LENGTH: 23
<212> TYPE: DNA
<213> ORGANISM: Artificial Sequence
<220> FEATURE:
<223> OTHER INFORMATION: Synthetic Construct

<400> SEQUENCE: 10
accagaggaa attttcaata ggc                                       23

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
aagggctcat gaccacagtc                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ttcagctctg ggatgacctt                                           20
```

PHARMACEUTICAL COMPOSITION FOR PREVENTING OR TREATING DEMENTIA AND IMPROVING COGNITIVE FUNCTION, COMPRISING GLASSWORT EXTRACT

TECHNICAL FIELD

The present invention was made with the support of the Ministry of Agriculture, Food and Rural Affairs of the Republic of Korea, under Project No. 116018-3, which was conducted under the research project entitled "High value-added food technology development project" within the project named "Development of cognitive ability-improving functional and food substitute material using phytomeal (halophyte-desalted material) and strategic export commercialization thereof" by Phyto Corporation under the management of the Korea Institute of Planning and Evaluation for Technology in Food, Agriculture, and Forestry, from 7 Jul. 2016 to 31 Dec. 2018.

This application claims priority to and the benefit of Korean Patent Application No. 10-2017-0059906 filed in the Korean Intellectual Property Office on 15 May 2017, the disclosure of which are incorporated herein by reference.

The present invention relates to a pharmaceutical composition containing a *Salicornia* spp. extract for prevention or treatment of dementia and improvement of cognitive ability and, more specifically, to a pharmaceutical composition containing a *Salicornia* spp. extract comprising acanthoside B as an active ingredient for prevention or treatment of dementia and improvement of cognitive ability and a method for preparing the same.

BACKGROUND ART

Dementia is defined as declines in memory and cognitive ability to impair daily life, and Alzheimer's disease (AD) is a clinicopathologically neurodegenerative disease involving the loss of memory and cognitive ability and the mental and behavioral disorders. This disease is the major cause of senile dementia, and 20-50% of AD cases occur in the elderly population over 85 years of age. Since AD requires long-term treatment and, due to the nature of the disease, also calls for social support for patient's family and of caregivers, the cost of treatment is estimated to reach $64 billion globally according to the report in 2010. Already in many developed countries, dementia is considered as a disease imposing a serious economic burden on patients, families, and society. A precise mechanism of this disease has not been elucidated yet, and the disease has a complicated onset mechanism due to the nature thereof, and thus there are many difficulties in the development of therapy.

There are various evidences that memory decline, one of the symptoms of dementia, is associated with the content of acetylcholine as a neurotransmitter. After the fact that the secretion of acetylcholine and the number of cholinergic neurons are reduced in the brain of dementia patients has been proved, it has become accepted that symptoms of dementia can be treated by inhibiting the acetylcholine degrading enzyme to increase acetylcholine on the basis of the assumption of "cholinergic deficient hypothesis", that is, the symptoms of dementia result from the reduction of acetylcholine in the neuron presynapses. It has also been reported that as the concentration of acetylcholine esterase (ACHE) increases in the cerebral blood vessels, cholinergic neurotransmitters for neurons are deficient, thus causing memory and cognitive impairment. Currently, four FDA-approved medicines for treatment are tacrine (Cognex), donepezil (Aricept), rivastigmine (Exelon), and galantamine (Reminyl), all which are acetylcholine esterase (AChE) inhibitor compounds. In addition to the four medicines approved by the FDA, many medicines are currently under clinical trials. However, Tacrine is scarcely used at present due to side effects thereof, such as drug toxicity and hepatotoxicity, although it is a drug showing strong acetylcholine esterase inhibitory activity, and Rivastigmine is known to have disadvantages in that it may cause vomiting and dizziness and is difficult to administer at high doses effective for therapy. Therefore, the development of an AChE inhibitor of a natural material, which will substitute for a chemical synthetic drug and has no side effects and toxicity, is urgently required, and studies related to the prevention of dementia and the development of medicines using a new AChE inhibitor compound derived from natural materials are also actively being conducted. Recently, the development of next-generation AChE inhibitors enabling intradermal or intravenous injection is being conducted.

Meanwhile, neuroinflammation is known to be involved in pathological mechanisms of neurological diseases, such as Alzheimer's dementia, senile dementia, Parkinson's disease, multiple sclerosis, and AIDS dementia, and inflammation responses by hypersensitization of microglia and astrocytes are receiving attention as major causes and effects of Parkinson's disease, which is one of the representative neurodegenerative diseases. The neuroglia is one type of important cells that constitute the central nervous system. Appropriately activated neuroglia and well-regulated inflammation responses have neuron and tissue protective actions. However, when these cells are not properly regulated due to excessive inflammation responses, the inflammation mediators produced by these cells may exhibit neuronal cytotoxicity and cause degenerative mutations of nerve tissue.

Degenerative diseases of the brain and nervous system are generic terms of diseases in which specific neuronal groups of the brain and spinal cord lose their functions and the number of neurons is decreased, and representative examples thereof are Alzheimer's disease (AD), Parkinson's disease, and Huntington's disease (HD). Through molecular biology and immunohistochemical staining studies that have been accumulated over the past 30 years, neurodegenerative diseases are known to occur due to the apoptosis of neurons, which are most important in the information transmission of the brain and nervous system: problems in the formation or functions of synapses that transmit information between brain cells: and an abnormal increase or decrease in electrical activity of brain nerve, and these phenomena increase further with age. At present, the aging of the population is rapidly progressing in the world, especially in emerging economies and western countries. In Korea, the number of elderly people aged 65 and over was over 8 million in 2015, accounting for 15.7% of the total population, and it is predicted to reach 40.1% by 2060.

Meanwhile, the major features of AD brain lesions are microgliosis and neuroinflammation, and according to numerous epidemiologic studies, the long-term taking of NSAID-based anti-inflammatory drugs showed a tendency of lowering the prevalence of AD. A 10-year long-term project in Canada also showed a reduced prevalence of AD when patients with mild cognitive impairment received NSAID treatment. It is therefore expected that a neuroinflammation inhibitor can be used as an effective preventive and treating agent in the events of mild and moderate cognitive impairments. However, considering a case in which the COX-2 inhibitor "Prexige" (lumiracoxib), as an inflammation medicine, by Novartis has been prohibited due to side effect thereof in Canada and Australia, the development of AD preventive and treating agents using neuroinflammation inhibiting drugs or brain cell protecting drugs with fewer side effects from natural materials instead of conventional chemical synthetic drugs are recently receiving attention.

*Salicornia* spp. are annual herbs belonging to the Chenopodiaceae family, and are obligatory halophytes or true halophytes, which can be grown without growth reduction even in a sand culture with 200 mM NaCl due to strong salt resistance thereof among halophytes and absolutely require salts for growth. In obligatory halophytes or true halophytes, solutes contributing to osmotic control are known to be osmosis resistant organic substances, and representative osmosis resistant substances accumulated in cells are amino acids, onium compounds, such as proline and glycine betaine, sugar alcohols, such as mannitol, sorbitol, and inositol, monosaccharide trehalose, and the like. *Salicornia* spp. need no "fertilizer" since they feed on seawater and require no "agricultural pesticides" since they are not damaged by diseases and insects due to high salinity in the body, and thus *Salicornia* spp. are environmentally friendly/sustainable crops. *Salicornia* spp. are naturally grown or cultivated all over the world including Korea, USA, and Europe. *Salicornia* spp. can be cultivated in triplicate for one year especially in the subtropical and tropical regions, and therefore *Salicornia* spp. are optimal model plants for "Seawater Agriculture" suitable for water shortage and food shortage due to global warming.

*Salicornia* spp. are also known as "reservoirs of minerals" since they contain large amounts of vegetable salts (NaCl, KCl, etc.), calcium, magnesium, potassium and the like in the body. *Salicornia* spp. have large amounts of nutrients, such as dietary fibers and essential amino acids, and are rich in physiologically active plant substances, such as chlorophyll, polyphenol and flavonoids, and thus have long been used as a folk remedy for the removal of toxins and fecal stasis accumulated in the body and for the treatment of cancer, hypertension, diabetes, hepatitis, skin diseases, arthritis and the like. As research on physiologically active substances from native plants has been active in Korea for the past 10 years, studies on functionalities of the halophyte *Salicornia* spp., which have been naturally grown in the west coast of Korea, have been activated by Korean researchers, and as a result, more than 100 Korean and oversea academic papers and numerous patents have been derived. In particular, choline of *Salicornia* spp. is known to be an important precursor of acetylcholine as a neurotransmitter, sphingomyelin as a constituent for neurons in the brain, and lecithin as a constituent of body constituent cells, and betaine is a substance that plays a major role in detoxification in the liver and is known to be a crucial contributor to reducing blood toxicity by eliminating toxicity in the body.

*Salicornia* spp. contain large amounts of salts (more than 35%) as raw materials per se, and thus are utilized as a salt substitute while keeping salty taste in *Salicornia* spp. related products (powder, extract, pills, and the like) or developed as slightly salted products through mixing with other raw materials. In spite of the research of a variety of functionality of *Salicornia* spp., *Salicornia* spp., extracts or powders contain a high concentration of sodium, and thus there was a limitation in the production of functional materials from 100% *Salicornia* spp. powders or 100% *Salicornia* spp. extracts. The present inventors have source techniques for functionality-enhanced desalted *Salicornia* spp. materials through desalination and for manufacturing methods therefor.

The present invention verified excellent acetylcholine esterase inhibitory activity of the desalted *Salicornia* spp. extracts; isolated acanthoside B, as an active ingredient, from the extracts; and verified cytoprotective activity through the inhibition of neuroinflammation and improvement effects of memory and cognitive ability in amnesia animal models by the *Salicornia* spp. extracts and acanthoside B. Therefore, the present invention supposes a pharmaceutical composition and a functional food each containing, a desalted *Salicornia* spp. extract or acanthoside B as an active ingredient for prevention or treatment of dementia and improvement of cognitive ability.

DETAILED DESCRIPTION OF THE INVENTION

Technical Problem

The present inventors endeavored to develop an agent for prevention or treatment of dementia as a neuroinflammation inhibiting medicine having fewer side effects. As a result, the present inventors isolated acanthoside B from a *Salicornia europaea* extract, and verified that said compound shows cytoprotective activity through the inhibition of neuroinflammation and improvement effects of memory and cognitive ability in amnesia animal models, and thus the present inventors completed the present invention.

Therefore, an aspect of the present invention is to provide a pharmaceutical composition for prevention or treatment of dementia or improvement of cognitive ability.

Another aspect of the present invention is to provide a functional food or a feed composition for improvement of cognitive ability and memory.

Still another aspect of the present invention is to provide a method for isolating acanthoside B.

Still another aspect of the present invention is to provide a method for treatment of dementia.

Still another aspect of the present invention is to provide a method for enhancement or improvement of cognitive ability.

Technical Solution

In accordance with an aspect of the present invention, there is provided a pharmaceutical composition for prevention or treatment of dementia or improvement of cognitive ability, the pharmaceutical composition containing acanthoside B represented by chemical formula 1 below or a pharmaceutically acceptable salt thereof.

[Chemical Formula 1]

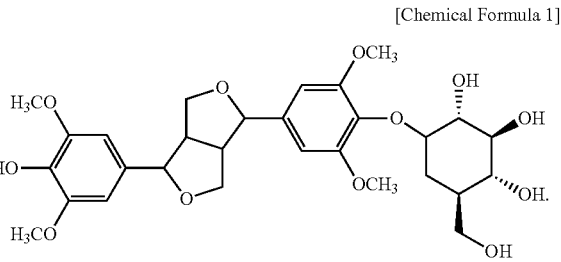

The present inventors endeavored to develop an agent for prevention or treatment of dementia as a neuroinflammation inhibiting medicine having fewer side effects. As a result, the present inventors isolated acanthoside B from a *Salicornia europaea* extract, and verified that said compound shows cytoprotective activity through the inhibition of neuroinflammation and improvement effects of memory and cognitive ability in amnesia animal models.

The present inventors freeze-dried and then pulverized *Salicornia europaea*, followed by desalination using cold water, and performed hot-water extraction or enzymatic degradation extraction on the desalted powder, followed by organic solvent fractionation using chloroform and then column chromatography. After that, the present inventors isolated a single substance by HPLC, and then performed structural analysis thereof. As a result, the present inventors identified the singe substance as acanthoside B and verified cytoprotective activity thereof.

Various *Salicornia* spp. may be used, and for example, one or more *Salicornia* spp. selected from the group consisting of *Salicornia europaea, Salicornia perennans, Salicornia procumbens, Salicornia persica, Salicornia maritima, Salicornia bigelovii, Salicornia depressa, Salicornia rubra, Salicornia praecox, Salicornia senegalensis, Salicornia perrieri, Salicornia pachystachya, Salicornia meyeriana, Salicornia uniflora* and *Salicornia brachiate* may be used.

A target disease of the present invention, "dementia", includes Alzheimer-type dementia, cerebrovascular dementia, neuroinflammatory dementia, degenerative brain diseases [e.g., dementia with Lewy bodies (DLB), multi-infarct dementia (MID), frontotemporal lobar degeneration (FTLD), Pick's disease, corticobasal degeneration (CBD), progressive supranuclear palsy (PSP), Parkinson's disease and Huntington's disease], and the like, but is not limited thereto.

In the present invention, the pharmaceutical composition for improvement of cognitive ability may be used in the same meaning as a pharmaceutical composition for enhancement of cognitive ability or a pharmaceutical composition for amelioration of memory disorders or enhancement of memory.

As used herein, the term "containing as an active ingredient" refers to the inclusion of an amount that is sufficient to attain efficacy or activity of acanthoside B below. Acanthoside B contained in the composition of the present invention is a compound isolated from *Salicornia* spp., which are natural plant materials, and the quantitative upper limit thereof contained in the composition of the present invention may be selected within an appropriate range by a person skilled in the art.

Here, the acanthoside B used as an active ingredient may be used as itself or in a form of a salt, preferably a pharmaceutically acceptable salt.

The salt is preferably an acid addition salt formed by a pharmaceutically acceptable free aid.

The free acid may be an inorganic acid and an organic acid.

Examples of the organic acid include citric acid, acetic acid, lactic acid, tartaric acid, maleic acid, fumaric acid, formic acid, propionic acid, oxalic acid, tripleuroacetic acid, benzoic acid, gluconic acid, methanesulfonic acid, glycolic acid, succinic acid, 4-toluenesulfonic acid, glutamic acid and aspartic acid, but are not limited thereof.

Examples of the inorganic acid include hydrochloric acid, bromic acid, sulfuric acid and phosphoric acid, but are not limited thereto.

The pharmaceutical composition of the present invention may contain a pharmaceutically acceptable carrier.

The pharmaceutically acceptable carrier is normally used at the time of formulation, and examples thereof may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate and mineral oil, but are not limited thereof.

The pharmaceutical composition of the present invention may further contain a lubricant, a wetting agent, a sweetening agent, a flavoring agent, an emulsifier, a suspending agent, a preservative and the like, in addition to the above ingredients.

Suitable pharmaceutically acceptable carriers and agents are described in detail in *Remington's Pharmaceutical Sciences* (19th ed., 1995).

The pharmaceutical composition of the present invention may be administered orally or parenterally.

Examples of parenteral administration may include intravenous injection, subcutaneous injection, intramuscular injection, intraperitoneal injection and transdermal administration.

The appropriate dose of the pharmaceutical composition of the present invention varies depending on factors, such as a formulating method, a manner of administration, patient's age, body weight, gender and morbidity, food, a time of administration, a route of administration, an excretion rate, and response sensitivity.

An ordinarily skilled practitioner can easily determine and prescribe an effective dose for desired treatment or prevention.

According to a preferable embodiment of the present invention, the daily dose of the pharmaceutical composition of the present invention is 0.001-10000 mg/kg.

The pharmaceutical composition of the present invention may be formulated into a unit dosage form or may be prepared in a multi-dose container by using a pharmaceutically acceptable carrier and/or excipient according to a method that is easily conducted by a person having an ordinary skill in the art to which the present invention pertains.

Here, the dosage form may be a solution in an oily or aqueous medium, a suspension, an emulsion, an extract, a powder, granules, a tablet or a capsule, and may further contain a dispersant or a stabilizer.

In accordance with another aspect of the present invention, there is provided a functional food or a feed composition containing acanthoside B represented by chemical formula 1 below for improvement of cognitive ability and memory.

[Chemical Formula 1]

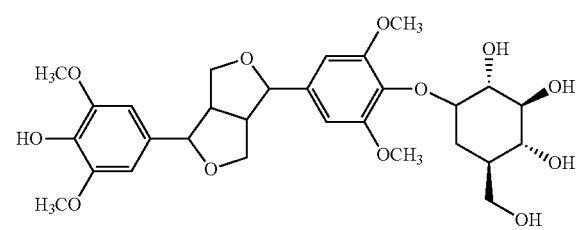

The functional food or feed composition for improvement of cognitive ability and memory of the present invention uses acanthoside B, which is the same active ingredient as in the pharmaceutical composition for prevention or treatment of dementia or improvement of cognitive ability, and descriptions of overlapping contents therebetween are omitted to avoid excessive complication of the specification.

The composition of the present invention, if a food composition, may be prepared in the form of a powder, granules, a tablet, a capsule or a drink.

Examples thereof are various foods such as candies, drink, gum, tea, vitamin complexes or dietary food supplements.

The food composition of the present invention may contain not only acanthoside B as an active ingredient but also the ingredients that are normally added at the time of food manufacturing, for example, a protein, a carbohydrate, a fat, a nutrient, seasoning and a flavoring agent.

Examples of the foregoing carbohydrate may include ordinary sugars (monosaccharides, such as glucose and fructose; disaccharides, such as maltose, sucrose, and oligosaccharides; and polysaccharides, such as dextrin and cyclodextrin) and sugar alcohols, such as xylitol, sorbitol, and erythritol. Examples of the flavoring agent may include natural flavoring agents (thaumatin, and stevia extract (e.g., rebaudioside A, glycyrrhizin, etc.)) and synthetic flavoring agents (saccharin, aspartame, etc.).

For example, the food composition of the present invention, when being manufactured into a drink, may further contain, in addition to acanthoside B of the present invention, citric acid, liquefied fructose, sugar, glucose, acetic acid, malic acid, fruit juice, an *Eucommia ulmoides* extract, a jujube extract and a licorice extract.

Meanwhile, *Salicornia* spp. have long been used for an edible purpose and as a folk drug, and thus the ingredients extracted from *Salicornia* spp. or *Salicornia* spp. per se could be expected to have no toxicity and side effect. For the same reasons, a *Salicornia* spp. extract or a fraction ingredient thereof can also be developed as an animal medicine and a functional feed for the same purposes.

In accordance with still another aspect of the present invention, there is provided a pharmaceutical composition containing a *Salicornia* spp. extract for prevention or treatment of dementia or improvement of cognitive ability.

In accordance with still another aspect of the present invention, there is provided a functional food or a feed composition containing a *Salicornia* spp. extract for improvement of cognitive ability and memory.

The *Salicornia* spp. extract defined herein uses desalted *Salicornia* spp. as a raw material.

According to an embodiment of the present invention, *Salicornia* spp. may be desalted by mixing a dried powder of *Salicornia* spp. with cold water. According to a specific embodiment of the present invention, a desalted *Salicornia* spp. product (e.g., a desalted powder) can be obtained by washing *Salicornia* spp., followed by freeze-drying, hot-air drying, or drying in the shade, followed by smashing, and then desalting the obtained dried powder using cold water at 3-9□.

The *Salicornia* spp. extract defined herein can be extracted by using desalted *Salicornia* spp. as a raw material and employing water, a C1 to C4 lower alcohol, or a mixture solvent thereof. Examples of the C1 to C4 lower alcohol include methanol, ethanol, propanol, butanol, iso-propanol, and the like.

According to an embodiment of the present invention, the *Salicornia* spp. extract includes an extract obtained by enzymatic hydrolysis of desalted *Salicornia* spp. before extraction and then extraction with water or an ethanol mixture solvent.

Examples of an enzyme used in the enzymatic hydrolysis include cellulase, hemicellulase, pectinase, β-glucanase and a combination thereof, but are not limited thereto.

According to another embodiment of the present invention, the *Salicornia* spp. extract can be obtained by subjecting desalted *Salicornia* spp. to extraction using water or 50-100 (v/v) % of a C1 to C4 lower alcohol.

According to still another embodiment of the present invention, the *Salicornia* spp. extract can be obtained by subjecting a desalted *Salicornia* spp. enzymatic hydrolysate to extraction using water or 50-100 (v/v) % of a C1 to C4 lower alcohol. According to a particular embodiment of the present invention, the *Salicornia* spp. extract may be a 50% ethanol (v/v, %) extract of the desalted *Salicornia* spp. enzymatic hydrolysate (water:ethanol=1:1, v/v).

According to still another embodiment of the present invention, the *Salicornia* spp. extract may be (i) a polar solvent extract, (ii) an enzymatic hydrolysis extract, or (iii) an alkaloid fraction of *Salicornia* spp., which is to be described in a method for isolating acanthoside B below.

In accordance with still another aspect of the present invention, there is provided a method for isolating acanthoside B, the method including the steps of:

(a) obtaining (i) a polar solvent extract or (ii) an enzymatic hydrolysis extract from *Salicornia* spp.;

(b) adding an acidic solution to the resultant product in step (a), followed by stirring and standing, to eliminate precipitates;

(c) adding a basic solution to the resultant product in step (b) and then adding a non-polar organic solvent thereto to obtain an alkaloid fraction; and (d) purifying the alkaloid fraction in step (c) to obtain acanthoside B as a single substance.

Hereinafter, the method for isolating acanthoside B of the present invention will be described in detail.

Step (a): Obtaining *Salicornia* spp. Extract

First, an appropriate solvent is added to *Salicornia* spp., thereby obtaining (i) a polar solvent extract or (ii) an enzymatic hydrolysis extract.

According to a particular embodiment of the present invention, the *Salicornia* spp. represent stems, leaves or stems/leaves thereof.

In the present invention, the extract is obtained by treating *Salicornia* spp. or a desalted *Salicornia* spp. product with a solvent.

For example, the desalted *Salicornia* spp. product (e.g., a desalted powder) can be obtained by washing *Salicornia* spp., followed by freeze-drying, hot-air drying or drying in the shade, followed by pulverizing, and then desalting the obtained dried powder using cold water at 3-9□.

Examples of the polar solvent used in the isolation method of the present invention include (i) water, (ii) an alcohol (preferably, methanol, ethanol, propanol, butanol, n-propanol, iso-propanol, n-butanol, 1-pentanol, 2-butoxyethanol or ethylene glycol), (iii) acetic acid, (iv) dimethylformamide (DMFO), and (v) dimethyl sulfoxide (DMSO), but are not limited thereto.

According to an embodiment of the present invention, the polar solvent is water or a 50-100 (v/v) % C1 to C4 lower alcohol.

Examples of the enzyme include cellulase, hemicellulase, pectinase, β-glucanase and a combination thereof, but are not limited thereto.

Step (b): Adding Acid Solution, Followed by Stirring and Standing, to Eliminate Precipitates Next, an acidic solution is added to the resultant product in step (a), followed by stirring and standing, to eliminate precipitates;

According to an embodiment of the present invention, an acidic solution is added to the *Salicornia* spp. extract obtained in step (a), followed by stirring and then standing at 1-10° C. for 5-18 hours.

According to another embodiment of the present invention, an acidic solution is added to the *Salicornia* spp. extract obtained in step (a), followed by stirring and then standing at 2-8° C. for 10-14 hours.

According to still another embodiment of the present invention, an acidic solution is added to the *Salicornia* spp. extract obtained in step (a), followed by stirring and then standing at 4° C. for 12 hours.

According to a particular embodiment of the present invention, hydrochloric acid is added to the *Salicornia* spp. extract obtained in step (a), followed by stirring and then standing at 4° C. for 12 hours. The precipitates generated during such a procedure are eliminated by centrifugation and filtration under reduced pressure.

In the present invention, the acidic solution may be a weak acid solution or a strong acidic solution.

For example, hydrochloric acid, acetic acid, sulfuric acid or the like may be used, but the acid solution is not limited thereto.

Step (c): Obtaining Alkaloid Fraction

Next, a basic solution is added to the resultant product in step (b), followed by reaction, and a non-polar organic solvent is sequentially added, thereby obtaining an alkaloid fraction.

According to an embodiment of the present invention, ammonia water is added to the resultant product in step (b) to adjust pH to 10 or higher, and then chloroform is added to conduct distributive fraction. Chloroform in a chloroform fraction is removed by a vacuum evaporator, followed by freeze-drying, thereby obtaining an alkaloid fraction of desalted *Salicornia* spp. (PM-AL).

In the present invention, the basic solution may be ammonia water or caustic soda (NaOH), but is not limited thereto.

Examples of the non-polar organic solvent used in the isolation method of the present invention include chloroform, hexane, ethyl acetate, butanol, acetone, acetonitrile, methyl acetate, fluoroalkane, pentane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, dichloromethane, 1,2-dichloroethane, aniline, diethyl amine, ether, carbon tetrachloride and THF, but are not limited thereto.

According to an embodiment of the present invention, the non-polar solvent is chloroform.

Step (d): Isolating Acanthoside B

Last, the alkaloid fraction in step (c) is purified to obtain acanthoside B as a single substance.

In step (d), the alkaloid fraction in step (c) can be isolated using high-performance liquid chromatography.

The present inventors identified a molecular structure of the compound purely isolated by the above method, and as a result, verified that the compound is acanthoside B (chemical formula 1).

In accordance with still another aspect of the present invention, there is provided a method for treatment of dementia, the method including a step for administering, to a subject, a pharmaceutical composition containing acanthoside B represented by chemical formula 1 below or a pharmaceutically acceptable salt thereof.

[Chemical Formula 1]

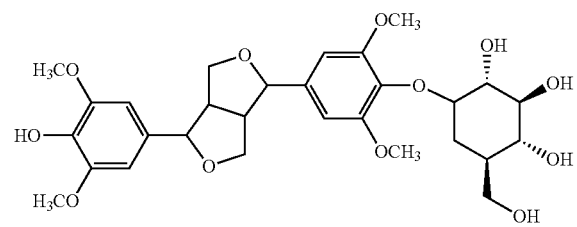

In accordance with still another aspect of the present invention, there is provided a method for improvement or amelioration of cognitive ability, the method including a step for administering, to a subject, a pharmaceutical composition containing acanthoside B represented by chemical formula 1 below or a pharmaceutically acceptable salt thereof.

[Chemical Formula 1]

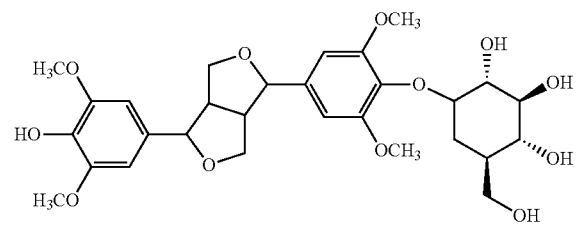

In accordance with still another aspect of the present invention, there is provided a method for improvement of cognitive ability and memory, the method including a step for administering, to a subject, a functional food or a feed composition containing acanthoside B represented by chemical formula 1 below.

[Chemical Formula 1]

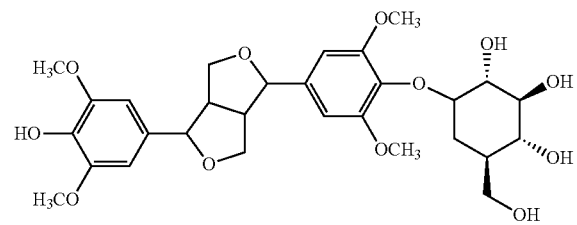

In accordance with still another aspect of the present invention, there is provided a method for treatment of dementia, the method including a step for administering, to a subject, a pharmaceutical composition containing a *Salicornia* spp. extract.

In accordance with still another aspect of the present invention, there is provided a method for improvement or amelioration of cognitive ability, the method including a step for administering, to a subject, a pharmaceutical composition containing a *Salicornia* spp. extract.

In accordance with still another aspect of the present invention, there is provided a method for improvement of cognitive ability and memory, the method including a step for administering, to a subject, a functional food or a feed composition containing a *Salicornia* spp. extract.

As used herein, the term "administration" refers to the provision of a certain material for a patient by any appropriate method, and the pharmaceutical composition of the present invention may be administered orally or parenterally through all general routes as long as the pharmaceutical composition can arrive at target tissues. In addition, the composition of the present invention may be administered using any apparatus that can deliver active ingredients to target cells.

As used herein, the term "subject" is not particularly limited, but means to encompass, for example, human, monkey, cow, horse, sheep, pig, chicken, turkey, quail, cat, dog, mouse, rat, rabbit or guinea pig, preferably a mammal, and more preferably a human being.

Advantageous Effects

Features and advantages of the present invention are summarized as follows.

(a) The present invention is directed to a pharmaceutical composition containing acanthoside B as an active ingredient for prevention or treatment of dementia or improvement of cognitive ability.

(b) It was verified in the present invention that a desalted *Salicornia* spp. extract and acanthoside B, which is an acetylcholine esterase inhibiting active ingredient isolated from the extract, had excellent neuronal protective activity through the inhibition of neuroinflammation, and significantly improved memory and spatial cognitive ability in the passive avoidance test and Y-maze test in memory decline animal models induced by scopolamine.

(c) The acanthoside B or *Salicornia* spp. extract of the present invention can be applied to a pharmaceutical composition for prevention or treatment of dementia, a pharmaceutical composition for improvement of cognitive ability, or a health functional food or feed for improvement of memory and cognitive ability.

MODE FOR CARRYING OUT THE INVENTION

Figure 1A:
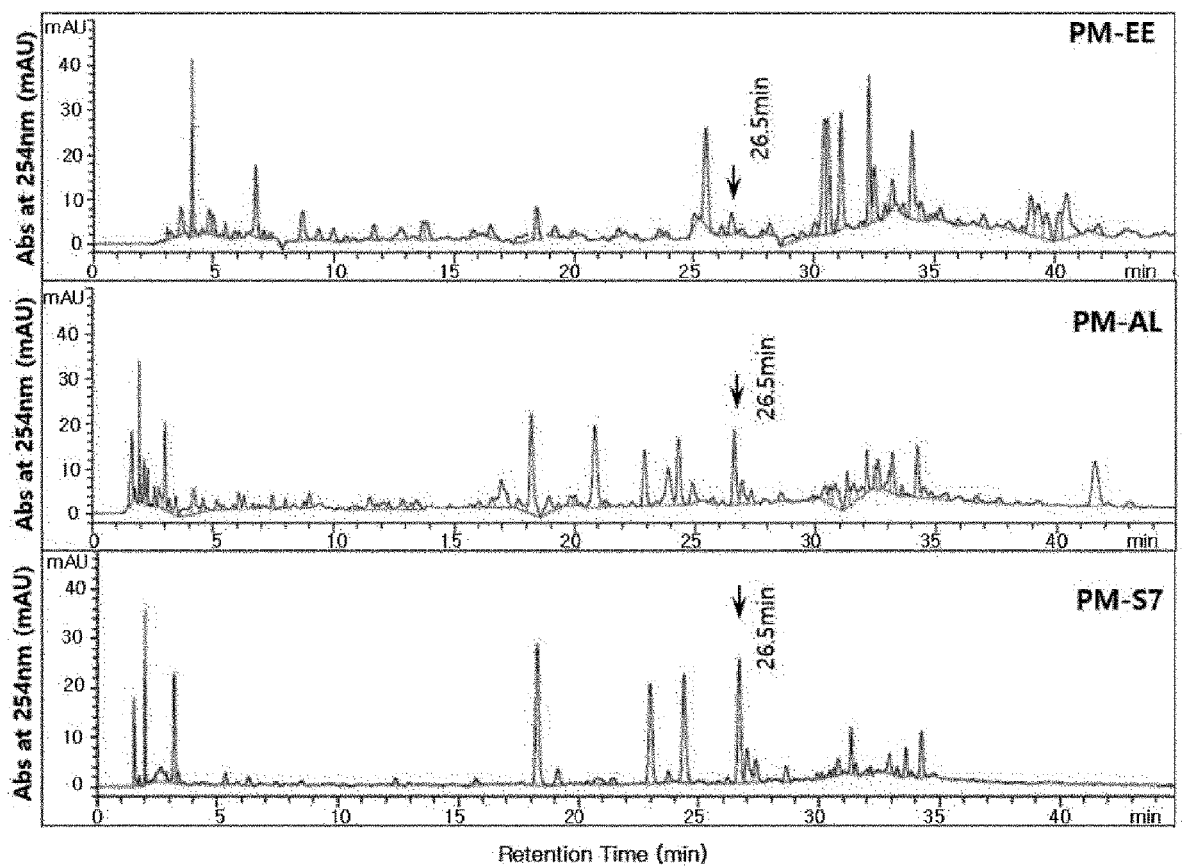
FIGS. 1a and 1b show: HPLC chromatogram comparison among main fractions and isolated compound S7-L3-3 (acanthoside B) compound during a purification procedure of an acetylcholine esterase inhibiting effective compound from a desalted *Salicornia* spp. extract (PM-EE); and the UV spectrum and chemical structure of S7-L3-3 (acanthoside B).

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Preparation of Various Extracts from Desalted *Salicornia europaea* Dried Powder Before *Salicornia europaea* cultivated in Shinan-gun, Jeollanam-do (Korea) have seeds in July to August, leaves and stems thereof were harvested, washed and dried. Various extracts were prepared from 10 g of a desalted *Salicornia europaea* powder prepared through a low-temperature cold-water desalting method.

For a hot-water extract, 100 mL of distilled water was added to 10 g of a desalted *Salicornia europaea* powder, followed by 15-minute ultrasonic treatment twice. Thereafter, reflux cooling extraction was performed at 100±1° C. for 1 hour. Then, the resultant extract was cooled and centrifuged (10,000 rpm, 25 minutes) to obtain a supernatant, which was then vacuum-concentrated and freeze-dried, to thereby prepare a hot-water extraction powder.

For methanol and ethanol extraction, 100 mL of methanol and ethanol were added to 10 g of a desalted *Salicornia europaea* powder, respectively, followed by 15-minute ultrasonic treatment twice. Thereafter, reflux cooling extraction was performed at around melting points of the respective solvents for 3 hours. Then, the resultant extracts were cooled, filtered under reduced pressure, and centrifuged (10,000 rpm, 25 minutes), to thereby obtain supernatants, respectively. The obtained supernatants were concentrated through drying under reduced pressure to remove alcohols, respectively, and then suspended in distilled water. The suspensions were freeze-dried to prepare methanol and ethanol extraction powders, respectively. In addition, for hydrolyzed alcohol extracts, water and methanol or water and ethanol were mixed at a (v/v) ratio of 1:1 or 3:7 to prepare 50% or 70% methanol or 50% and 70% ethanol, respectively, and then each 100 mL was added to 10 g of a desalted *Salicornia europaea* powder, respectively. Thereafter, 15-minute ultrasonic treatment was conducted twice, and then reflux cooling extraction was performed at about melting points of the solvents for 3 hours. Thereafter, the resultant extracts were cooled, filtered under reduced pressure, and centrifuged to obtain supernatants. The obtained supernatants were concentrated through drying under reduced pressure to remove alcohols, followed by freeze-drying, to thereby prepare 50% or 70% methanol and ethanol extraction powders.

Example 2: Preparation of Various Extracts from Desalted *Salicornia europaea* Enzymatic Hydrolysate

*Salicornia europaea* leaves and stems harvested in July to August were washed and dried. 60 mL of distilled water was added to 10 g of a desalted *Salicornia europaea* powder prepared through a low-temperature cold-water desalting method, followed by 15-minute ultrasonic treatment twice. Thereafter, cellulase, hemicellulase, pectinase and β-glucanase (Sigma Co, USA) each were added at 0.1% (v/v), followed by enzymatic hydrolysis at 50° C. for 18 hours, thereby obtaining a desalted *Salicornia europaea* enzymatic hydrolysate.

A hot-water extract of an enzymatic hydrolysate was prepared by adding 40 mL of distilled water to the desalted *Salicornia europaea* enzymatic hydrolysate and then carrying out reflux cooling extraction through the same method as in example 1.

Methanol and ethanol extracts of a desalted *Salicornia europaea* enzymatic hydrolysate were prepared as follows. 100 mL of methanol and ethanol were added to a dried powder obtained by freeze-drying the desalted *Salicornia europaea* enzymatic hydrolysate, followed by 15-minute ultrasonic treatment twice. Thereafter, reflux cooling extraction was performed at around melting points of the respective solvents for 3 hours. Then, the resultant extracts were cooled, filtered under reduced pressure, and centrifuged (10,000 rpm, 25 minutes), to thereby obtain supernatants. The obtained supernatants were concentrated through drying under reduced pressure to remove alcohols, and then suspended in distilled water. Thereafter, the suspensions were freeze-dried to prepare methanol and ethanol extraction powders of the desalted *Salicornia neuropaea* enzymatic hydrolysate.

50% methanol and 50% ethanol extracts of the desalted *Salicornia europaea* enzymatic hydrolysate were prepared by, after the enzymatic hydrolysis, adding an equivalent amount (60 mL, v/v=1:1) of methanol or ethanol and then carrying out extraction through the same method as in example 1. 70% methanol and 70% ethanol extracts of the desalted *Salicornia europaea* enzymatic hydrolysate were prepared by, after the enzymatic hydrolysis, adding 140 mL of methanol or ethanol and then carrying out extraction through the same as in example 1.

Example 3: Measurement of Acetylcholine Esterase Inhibitory Activity

It has been reported that as the concentration of acetylcholine esterase (AChE) increases in the cerebral blood vessels, cholinergic neurotransmitters for neurons are deficient in neurons, causing memory and cognitive impairment. Therefore, the measurement of AChE inhibitory activity can be used as a tool for the development of a drug or health functional raw material for prevention and treatment of dementia or enhancement of cognitive ability. In the present invention, the AChE inhibitory activity of a desalted *Salicornia europaea* extract, a desalted *Salicornia europaea* enzymatic hydrolysis extract, or purified fractions obtained from a desalted *Salicornia europaea* extract were measured, and the measurement was conducted by partially correcting Ellman's coupled enzyme assay. That is, 170 μL of 100 mM phosphate buffer (pH 8), 170 μL of 2 mM dithiobisnitrobenzoic acid (DTNB), and 20 μL of an extraction sample were added to on a 96-well microplate. Then, 20 μL of AChE 0.25 U/mL in the buffer was dispensed, followed by pre-incubation at 37° C. for 10 minutes, and then a 3.75 mM substrate solution of acetylcholine Iodide was added. The enzymatic reaction solution was incubated at 37° C. for 10 minutes, and then the absorbance was measured by a UV-VIS microreader at 410 nm. The AChE inhibitory activity was calculated as below by comparison between the absorbance (Ac) of a control group not containing a substrate and a sample and the absorbance (As) of a test group.

*AChE inhibitory activity (%)=[1−(As/Ac)]×100

Ac: absorbance of a control group,
As: absorbance of a sample group.

Test Example 1. Yields of Desalted *Salicornia europaea* Powder Extracts and AChE Inhibitory Activity Thereof The measurement results of AChE inhibitory activity of various desalted *Salicornia europaea* extracts prepared in example 1 at the same concentration (100 μg/mL) and the yields of the respective extracts are shown in Table 1.

TABLE 1

|  | Hot water | Methanol | Ethanol | 50% methanol | 50% ethanol | 70% methanol | 70% ethanol |
|---|---|---|---|---|---|---|---|
| Yeild (%) | 15.6 | 8.7 | 7.8 | 11.6 | 10.9 | 9.8 | 9.2 |
| AChE Inhibtory activity (%) | 52.6 | 58.9 | 61.2 | 62.5 | 65.2 | 60.5 | 62.8 |

* sample concentration: 100 μg/mL

As shown in Table 1 above, it could be verified that all of the hot-water extract, methanol and ethanol extracts, or hydrolyzed methanol and ethanol extracts of desalted *Salicornia europaea* showed high AChE inhibitory activity of 52.6% or higher at the concentration of 100 μg/mL. Especially, it could be seen that the 50% ethanol extract showed the highest AChE inhibitory activity (65.2%) and the hot-water extract showed the highest yield (15.6%).

Test Example 2. Yields of Desalted *Salicornia europaea* Enzymatic Hydrolysate and AChE Inhibitory Activity Thereof The measurement results of AChE inhibitory activity of various extracts of desalted *Salicornia europaea* enzymatic hydrolysate, prepared in example 2, at the same concentration (100 µg/mL) and the yields of the respective extracts are shown in Table 2.

TABLE 2

| — | Hot water | Methanol | Ethanol | 50% methanol | 50% ethanol | 70% methanol | 70% ethanol |
|---|---|---|---|---|---|---|---|
| Yeild (%) | 32.6 | 19.1 | 17.4 | 28.7 | 29.3 | 21.5 | 21.1 |
| AChE Inhibtory activity (%) | 54.0 | 60.9 | 65.2 | 62.7 | 66.4 | 61.8 | 63.6 |

* sample concentration: 100 µg/mL

As shown in Table 2 above, it could be verified that the hot-water extract, methanol and ethanol extracts, or hydrolyzed methanol and ethanol extracts of desalted *Salicornia europaea* enzymatic hydrolysate showed increased AChE inhibitory activity at the concentration of 100 µg/mL compared with the extracts before enzymatic hydrolysis. Furthermore, it could be particularly seen that the yields were remarkably increased. The reason seems that polymer dietary fibers in *Salicornia europaea* were hydrolyzed through actions of enzymes, such as cellulase, hemicellulose, pectinase, and β-glucanase, and therefore soluble components in water and alcohols were increased. Especially, the highest AChE inhibitory activity (67.2%) and a significant yield (29.3%) were shown in the 50% ethanol extract. Hence, 50% ethanol extraction on the desalted *Salicornia europaea* enzymatic hydrolysate was conducted for a mass-extraction condition for isolation of an active ingredient showing AChE inhibitory activity in the desalted *Salicornia europaea* extract.

Example 4: Isolation and Purification of Substance Having AChE Inhibitory Activity from Desalted *Salicornia europaea*

4-1. Preparation of Desalted *Salicornia europaea* Extract (PM-EE) and Alkaloid Fraction Thereof On the basis of the results of test examples 1 and 2, an active ingredient showing AChE inhibitory activity was isolated from the desalted *Salicornia europaea* extract. Leaves and stems of *Salicornia europaea* harvested in July to August were washed and freeze-dried. Thereafter, 3 L of distilled water was added to 500 g of a desalted *Salicornia europaea* powder obtained through cold-water desalination, followed by sufficient mixing. Then, a composite enzyme (Optivin Mash, Connell Bros Company, Australia) containing cellulose, hemicellulose, pectinase, and β-glucanase was added at 0.3% (v/v). In addition, enzymatic hydrolysis was conducted at 50° C. for 18 hours. An equivalent amount of ethanol was added to the produced enzymatic hydrolysate, and the mixture was subjected to reflux cooling extraction at 85±1° C. for 3 hours, followed by cooling. Then, centrifugation was conducted at 4° C. and 10,000 rpm for 25 hours. The obtained centrifuged supernatant was dried under reduced pressure at 45° C. to completely remove ethanol, followed by freeze-drying, thereby obtaining a desalted *Salicornia europaea* extract (PM-EE).

The obtained extract PM-EE (100 g) was dissolved in 2 L of distilled water, and then 6 N hydrochloric acid was added to adjust pH to 2.0. Then, the resultant solution was stirred for 30 minutes and allowed to stand at 4° C. for 12 hours. The precipitates generated during such a procedure were eliminated by centrifugation and filtration under reduced pressure. In addition, 6 N ammonia water was added to adjust pH to 10 or higher, and the resultant solution was transferred into a funnel, followed by distributive fraction using an equivalent amount of chloroform. An equivalent amount of chloroform was again added to a water layer, followed by second distributive fraction in the funnel. Thereafter, chloroform in the primary and secondary chloroform fractions was removed using a vacuum evaporator. Last, the fractions were suspended in distilled water, followed by freeze-drying, thereby obtaining an alkaloid fraction of desalted *Salicornia europaea* (PM-AL).

4-2: Column Chromatography Purification

The PM-AL fraction (8 g) obtained in example 4-1 was loaded a column (3.3×40 cm) charged with polar silica gel (60G, Merck, Germany). The fraction was released at a flow rate of 0.3 mL/min using a mobile solvent with different mixing proportions of chloroform and methanol. As a result, 100 mL of eight fractions (PM-1, PM-2, PM-3, PM-4, PM-5, PM-6, PM-7, and PM-8) were obtained. Of these, a fraction (PM-S7, 187 mg) having excellent AChE inhibitory activity was dried under reduced pressure, and then dissolved in 3 mL of methanol. Then, the solution was introduced into the third column (2.5×33 cm) charged with gel filtration Sephadex LH-20 for a low molecular weight, and then while 100% methanol (flow rate: 0.2 mL/min) as a mobile solvent is allowed to flow therethrough, a total of seven fractions (PM-7-L1, -L2, -L3, -L4, -L5, -L6, -L7). Finally, a PM-S7-L3 fraction, which has the most excellent AChE inhibitory activity among the seven fractions, was concentrated under reduced pressure, and freeze-dried to obtain 90 mg.

4-3. Pure Isolation by High Performance Liquid Chromatography (HPLC)

Figure 1B:
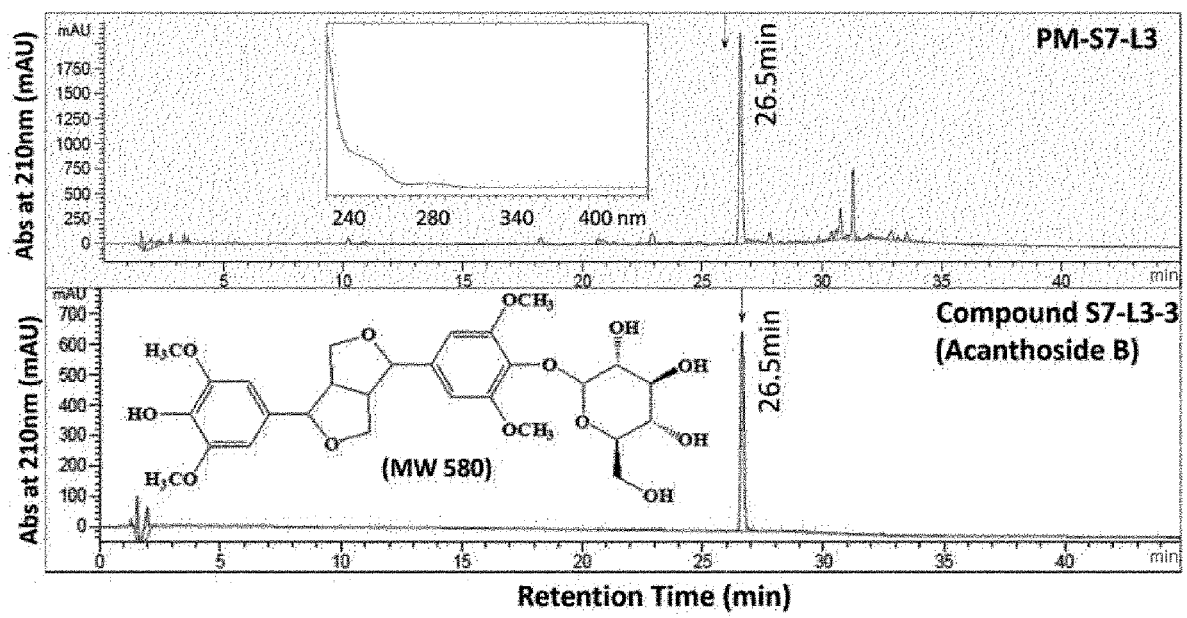
Figure 2:
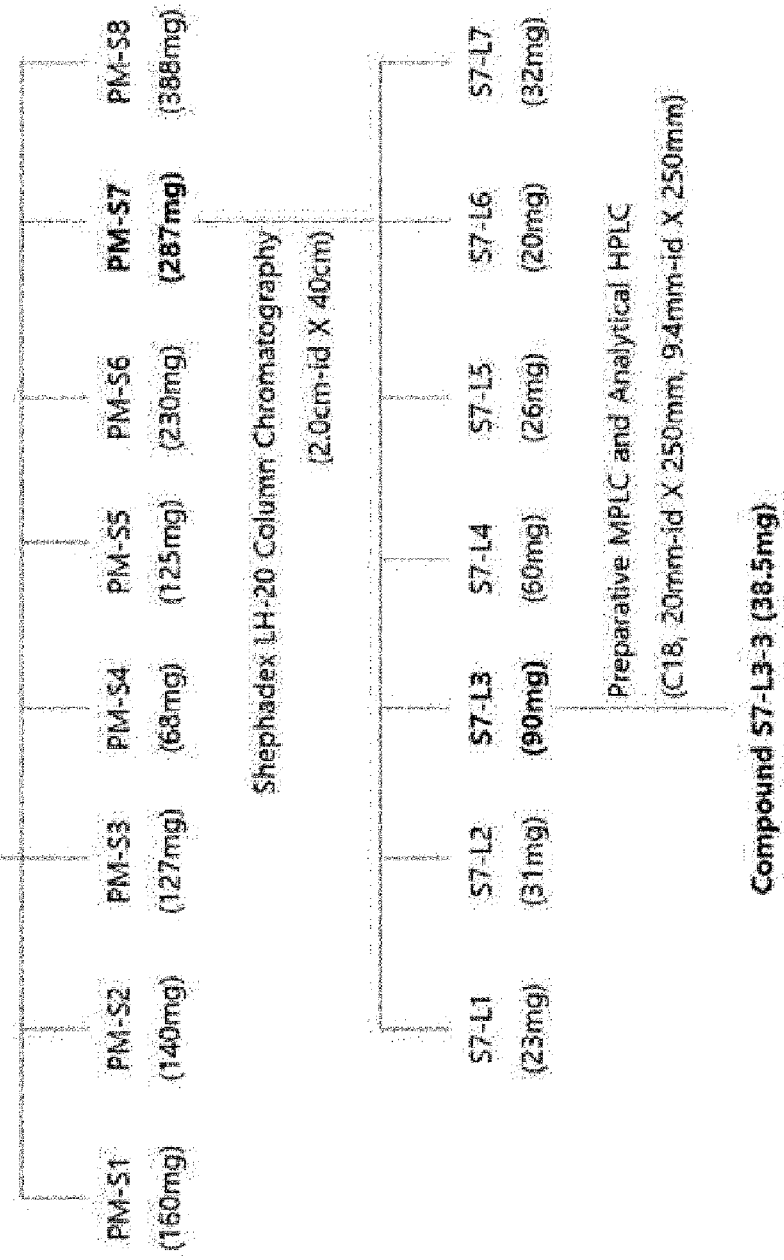
FIG. 2 is a schematic view of isolation and purification procedures of an AChE inhibiting effective compound from a desalted *Salicornia* spp. extract (PM-EE).

The PM-S7-L3 fraction (90 mg) obtained in example 4-2 was dissolved in 2 mL of methanol for HPLC, and filtered through a 0.22-µm filter, and then a single substance having strong AChE inhibitory activity (S3-L3-3) was isolated using analytical and preparative high-performance liquid chromatography. As analytical HPLC, a model (1260 Infinity, Agilent, USA) equipped with Zorbax Eclips C18 (5 µm, 4.5×250 mm, Agilent) was used. As preparative high-performance liquid chromatography, a model (Multiple Preparative HPLC (LC-forte/R, YMC, Japan)) equipped with a prep column (Triart C18, 20 mm×150 mm, 5 µm, YMC, Japan) was used. The mobile phase solvent conditions were as follows: the mobile phase solvent was allowed to flow through the column at a flow rate of 1 mL/min under gradient conditions using acetonitrile and tertiary distilled water containing 0.04% of trifluoroacetic acid (TFA). Agilent, 1200 DAD detector or YMC-YUV-3400 UV detector was used. As a result of pure fraction of compounds using absorbance at two wavelength regions (254 and 210 nm), compound S7-L3-1 (38.5 mg) could be obtained at a retention time of 26.5 minutes. In FIG. 1, analytical HPLC chromatogram profiles of the desalted *Salicornia europaea* extract (PM-EE), the column purification fractions PM-S7 and PM-S7-L3, and the compound S7-L3-3 isolated finally by analytical HPLC were compared, and it could be verified that as the purification proceeded, the intensity of the peak at 26.5 min, which corresponds to a retention time of the active ingredient S7-L3-3, was increased and the entire chromatogram was simplified. FIG. 1 shows the UV spectrum and chemical structure of acanthoside B, which were established by structural analysis of purely purified S7-L3-3. In addition, FIG. 2 shows a schematic diagram of the entire isolation and purification procedures of an AChE inhibiting active ingredient.

Figure 3:
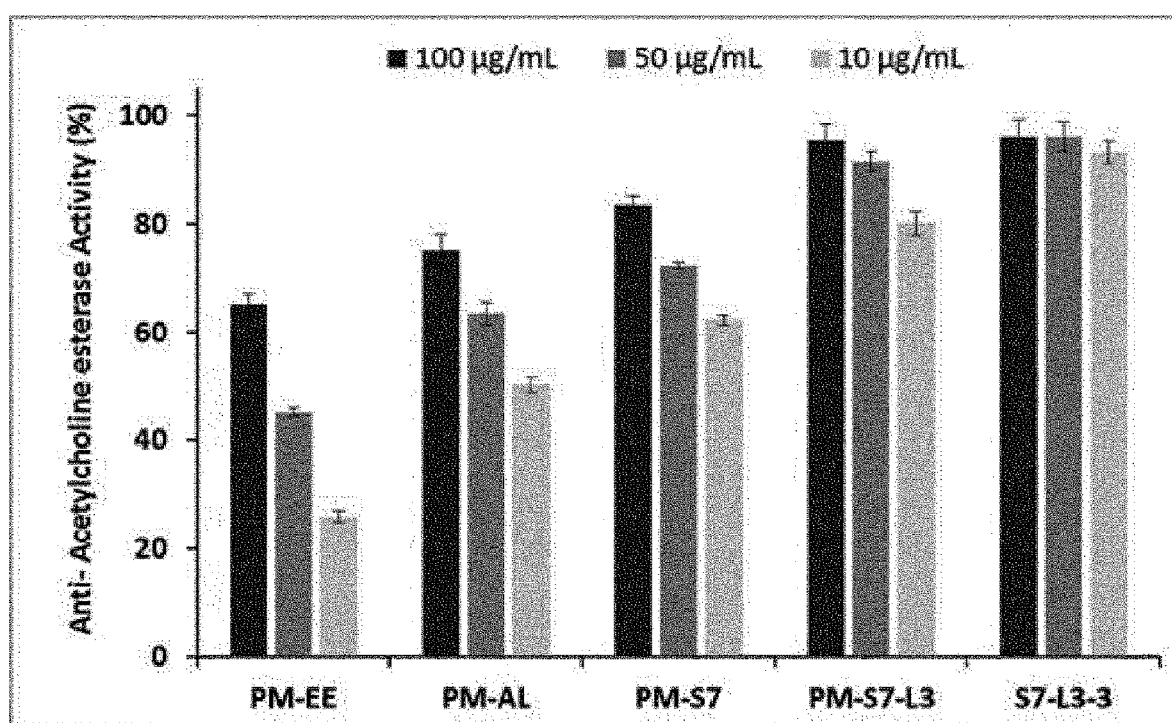
FIG. 3 shows AChE inhibitory activity comparison results among main fractions and the isolated compound S7-L3-3 (acanthoside B) during a purification procedure of an AChE inhibiting effective compound from a desalted *Salicornia* spp. extract (PM-EE).

4-4. Confirmation of AChE Inhibitory Activity and $IC_{50}$ Values of Desalted *Salicornia europaea* Extraction and Purification Fractions AChE inhibitory activity of the desalted *Salicornia europaea* extract (PM-EE), the alkaloid fraction of desalted *Salicornia europaea* (PM-AL), and the column chromatography purification fractions (PM-S7 and PM-S7-L3), and the finally isolated compound S7-L3-3, which were obtained during the purification procedure of the AChE inhibiting compound S7-L3-3 in examples 4-1 to 4-3 above, were compared and measured. The average values obtained from the test repeated three times or more at concentrations of 100, 50, and 10 µg/mL of each sample are shown in FIG. 3. The AChE inhibitory activity, 65.2%, of the desalted *Salicornia europaea* extract (PM-EE) at a concentration of 100 µg/mL was significantly excellent compared with a fermented *Aronia melanocarpa* extract first disclosed in Korean Patent Publication No. 10-2016-0088622. It could also be verified that as the purification proceeded, the AChE inhibitory activity of each fractions were gradually increased. It could be especially verified that at the concentration of 10 µg/mL, the AChE inhibitory activity of the finally purified compound S7-L3-3 was remarkably increased (93.2%) compared with that of PM-EE (25.8%). In addition, the $IC_{50}$ values of the extracts in respective steps and the purification fractions, at which the AChE inhibitory activity was reduced by 50%, were compared with those of galantamine as a positive control group, which is an AChE inhibiting synthetic medicine prescribed as a dementia drug, and berberine, which is an AChE inhibiting ingredient isolated from a natural material (Table 3). The structural analysis of example 5 below identified that the finally purified compound S7-L3-3 was acanthoside B. The measurement and comparison with eleutheroside E as a phenylpropanoid glycoside-based substance having a similar structure to acanthoside B is also shown in Table 3.

TABLE 3

| Sample name | $IC_{50}$ (µg/mL) |
|---|---|
| PM-EE | 78.9 ± 3.90 |
| PM-AL | 20.7 ± 1.23 |
| PM-S7 | 10.5 ± 0.8 |
| PM-S7-L3 | 4.4 ± 0.5 |
| S7-L3-3 (acanthoside B) | 2.8 ± 0.21 |
| Tacrine | 0.036 ± 0.01 |
| Galantamine | 3.6 ± 0.41 |
| Berberine | 10.7 ± 0.59 |
| Elutheroside E | 8.2 ± 0.37 |

As a result of measurement of AChE inhibitory activity $IC_{50}$ values of the respective samples, the desalted *Salicornia europaea* extract (PM-EE) showed a $IC_{50}$ value of 78.9±3.9, as shown in Table 3 above, and it could be verified that as the purification proceeded, such a value was gradually decreased. The finally purified S7-L3-3 (acanthoside B) showed an $IC_{50}$ value of 2.8±0.21, indicating that the AChE inhibitory activity increased by about 28 times due to the purification. The AChE inhibitory activity of S7-L3-3 (acanthoside B) was lower than that of tacrine ($IC_{50}$ value: 0.038±0.01), which is a drug which was initially prescribed as a FDA approved anti-dementia drug but for which clinical prescription is prohibited due to hepatotoxicity. However, the AChE inhibitory activity of S7-L3-3 (acanthoside B) was equal to or higher than that of the synthetic medicine galantamine ($IC_{50}$ value: 3.6±0.41) as an AChE inhibitor and was about 3.8 times better than that of the natural material-derived AChE inhibitory compound berberine ($IC_{50}$ value: 5.6±0.19). Meanwhile, eleutheroside E, which has a phenylpropanoid glycoside-based similar structure, like acanthoside B, and has one more glucose molecule than acanthoside B, was measured to have an $IC_{50}$ value of 8.2±0.37, indicating that the AChE inhibitory activity of S7-L3-3 (acanthoside B), which is a purified sample in the *Salicornia europaea* extract, was about three times stronger than that of eleutheroside E. Therefore, it could be seen that such a difference in AChE inhibitory activity between eleutheroside E and acanthoside B indicates that the degree of substitution of glucose in the phenylpropanoid molecule functions as an important factor in the AChE inhibitory activity. The AChE inhibitory activity of the *Salicornia europaea* extract (PM-EE, $IC_{50}$: 78.9±3.90) was also higher that the antecedently reported AChE inhibitory activity values of an *Aster yomena* extract [Kor. J. Herbology 2009; 24(4):121-126] and a fermented *Aronia melanocarpa* extract [Korean Patent Publication No. 10-2016-0088622], and therefore it was suggested that both of acanthoside B and the *Salicornia europaea* extract (PM-EE) are AChE inhibiting natural materials having no side effects and toxicity and can be developed for uses of a medicine and a functional food for prevention and treatment of dementia and improvement of cognitive ability.

Example 5: Structural Analysis of Compound (S7-L3-3) Isolated from Desalted *Salicornia europaea* Extract (PM-EE) Showing AChE Inhibitory Activity

5-1. Determination of Molecular Weight and UV λMax of S7-L3-3

Figure 4:
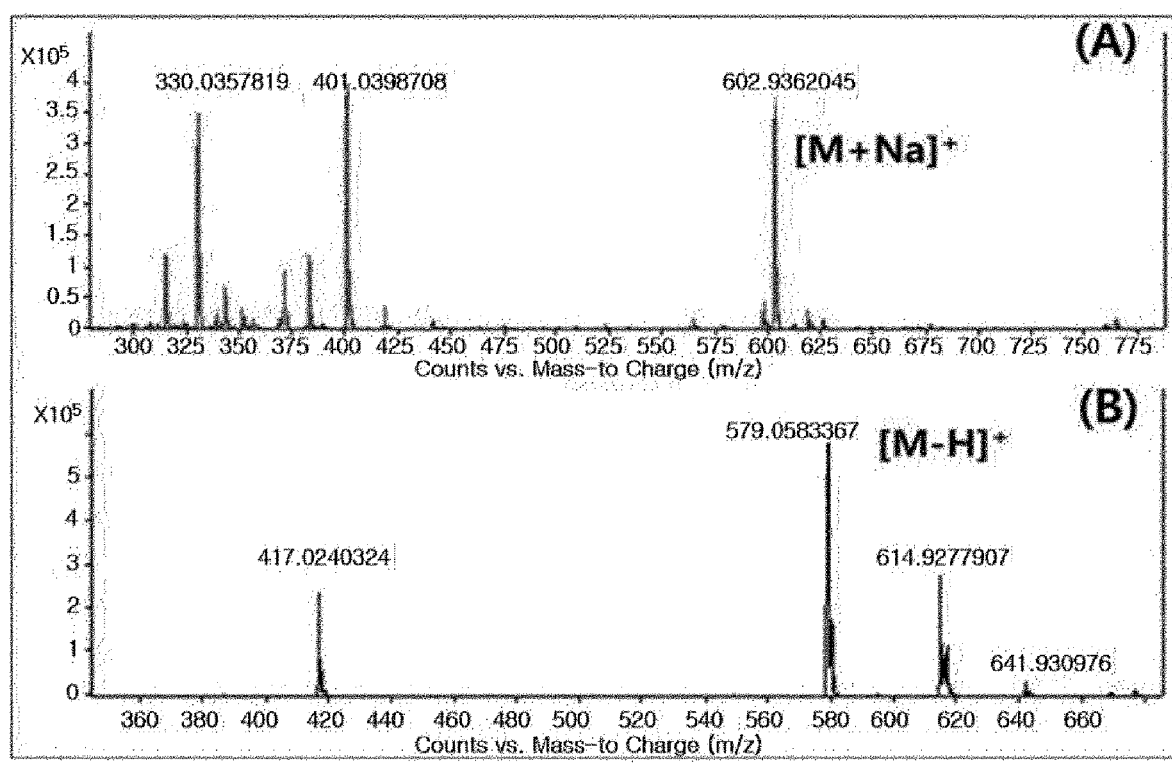
FIG. 4 shows ESI-MS spectra of the isolated compound S7-L3-3: (A) positive mode, (B) negative mode.

For determination of the molecular weight of S7-L3-3, the compound isolated in example 4-3, 1 mg of compound A was subjected to positive and negative scanning using an electrospray ionization (ESI) mass spectrometer (LC-ESI mass spectrometer, AGILENT 1100, USA Micromass Quattro II), and high-resolution MS was measured (FIGS. 4a and 4b). The maximum UV absorption range of the isolated compound S7-L3-3 was measured in the range of 190-400 nm using a UV spectrophotometer (Genesys 10S UV-VIS spectrophotometer, Thermo Scientific, USA) by dissolving the sample at a concentration of 1 mg/mL in methanol.

5-2. Nuclear Magnetic Resonance (NMR) Analysis

Figure 6A:
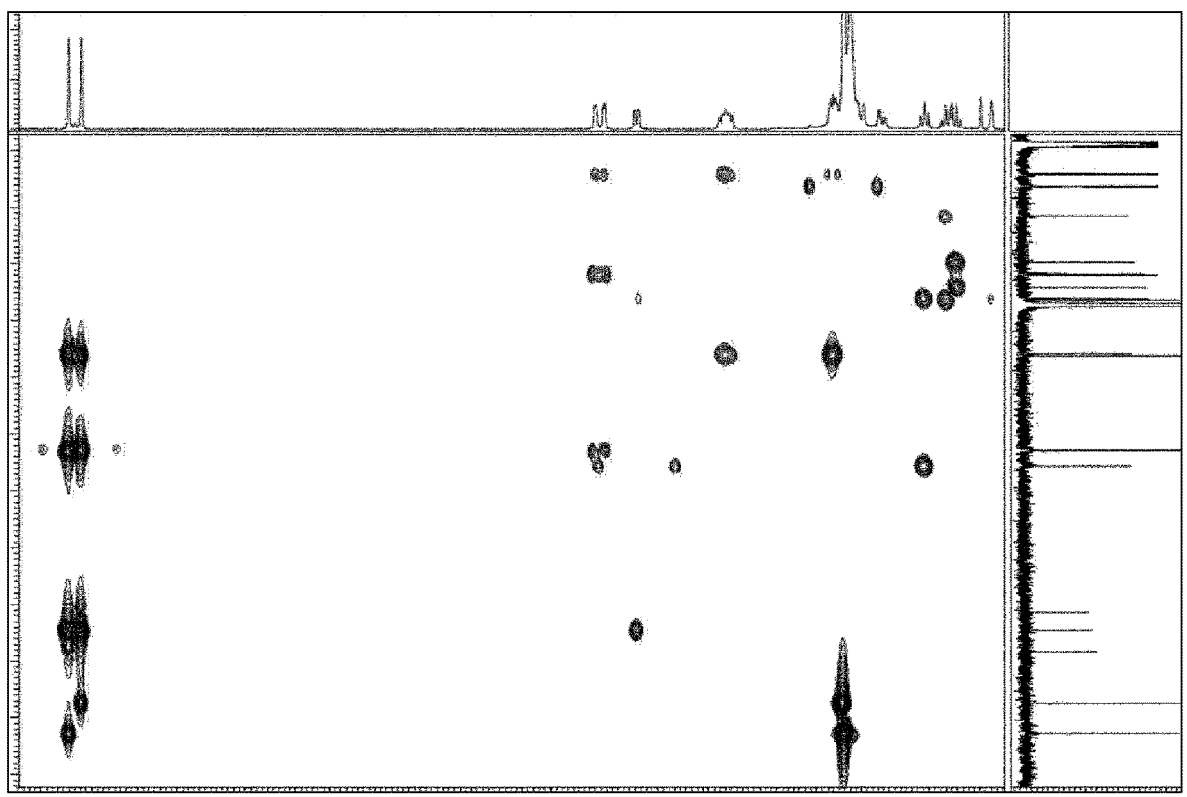
FIGS. 6a and 6b show HMBC-NMR (6a) and $^1$H—$^1$H COSY (6b) spectra of the isolated compound S7-L3-3.
Figure 6B:
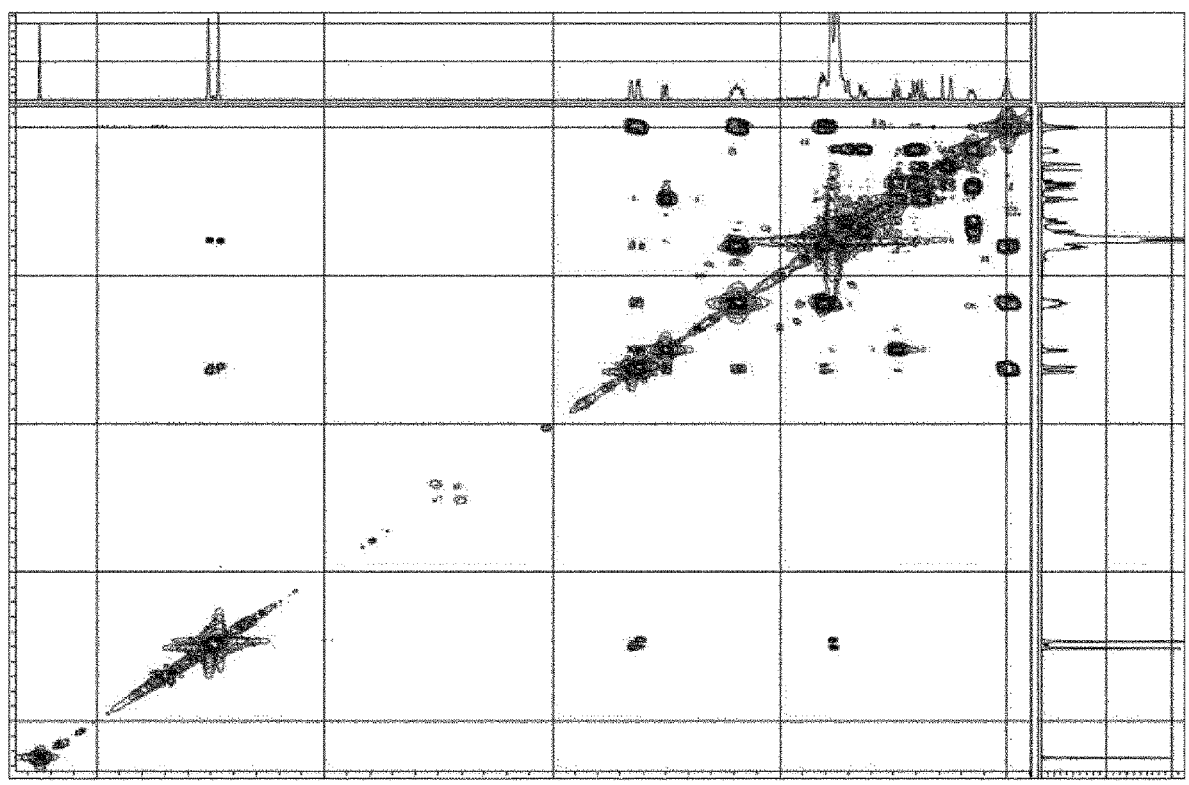
Figure 7:
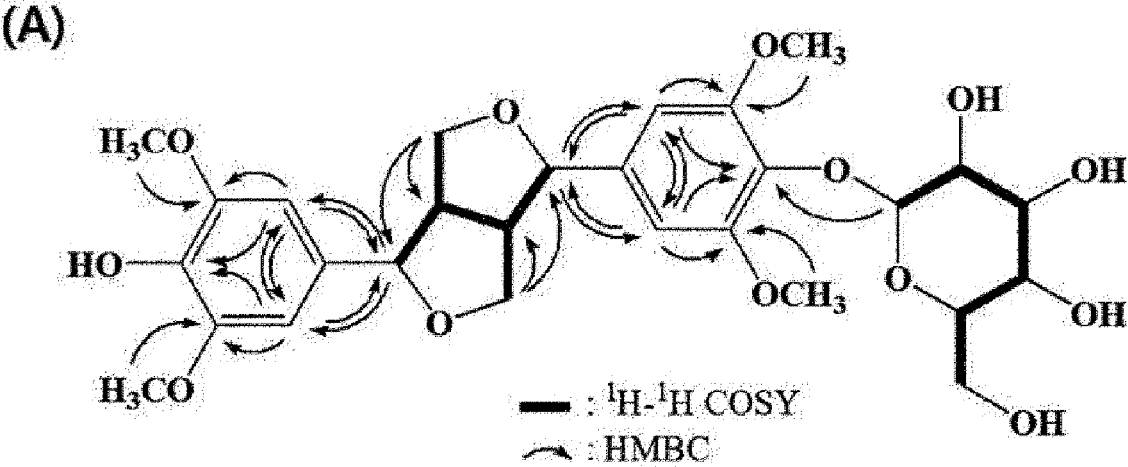
FIG. 7 shows a stereoscopic structure (A) of S7-L3-3 through $^1$H and $^{13}$C-NMR and 2D-NMR analysis and a chemical structure (B) of S7-L3-3 through intramolecular carbon and hydrogen positioning.
Figure 7:
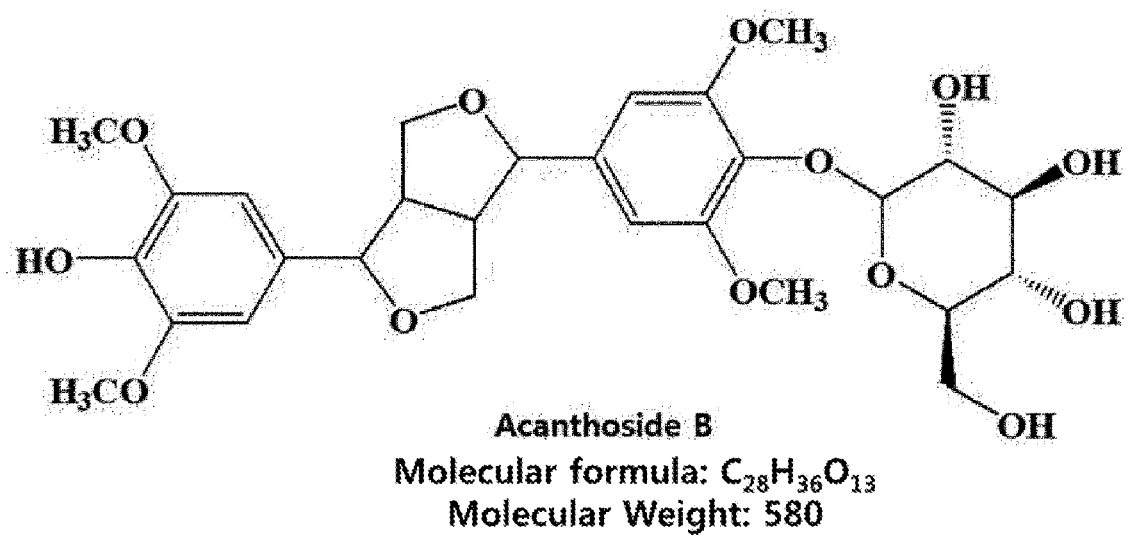

NMR spectroscopy was performed in a manner in which compound S7-L3-3 (5 mg) was completely dried, dissolved in $CDCl_3$ (0.5 ml), placed in a 5-mm NMR tube, and analyzed using a Jeol model (JNM-ECA 600, Jeol, Japan), and $^1$H-NMR (FIG. 5a) was measured at 600 MHz, and $^{13}$C-NMR (FIG. 5b) was measured at 150 MHz. Through HMBC-NMR (FIG. 6a) and $^1$H—$^1$H COSY-NMR (FIG. 6b) measurement, the positions and stereoscopic structure of hydrogen and carbon in the compound S7-L3-3 were determined (FIG. 7).

As a result of the measurement above, the compound S7-L3-3 was identified to be acanthoside B ((2S,3R,4S,5S,6R)-2-[4-[(3S,3aR,6S,6aR)-3-(4-hydroxy-3,5-dimethoxyphenyl)-1,3,3a,4,6,6a-hexahydrofuro [3,4-c]furan-6-yl]-2,6-dimethoxyphenoxy]-6-(hydroxymethyl)oxane-3,4,5-triol) having a molecular weight of 580, which has not been reported in Salicornia europaea until now, and the physical and chemical properties thereof are as follows.

Figure 5A:
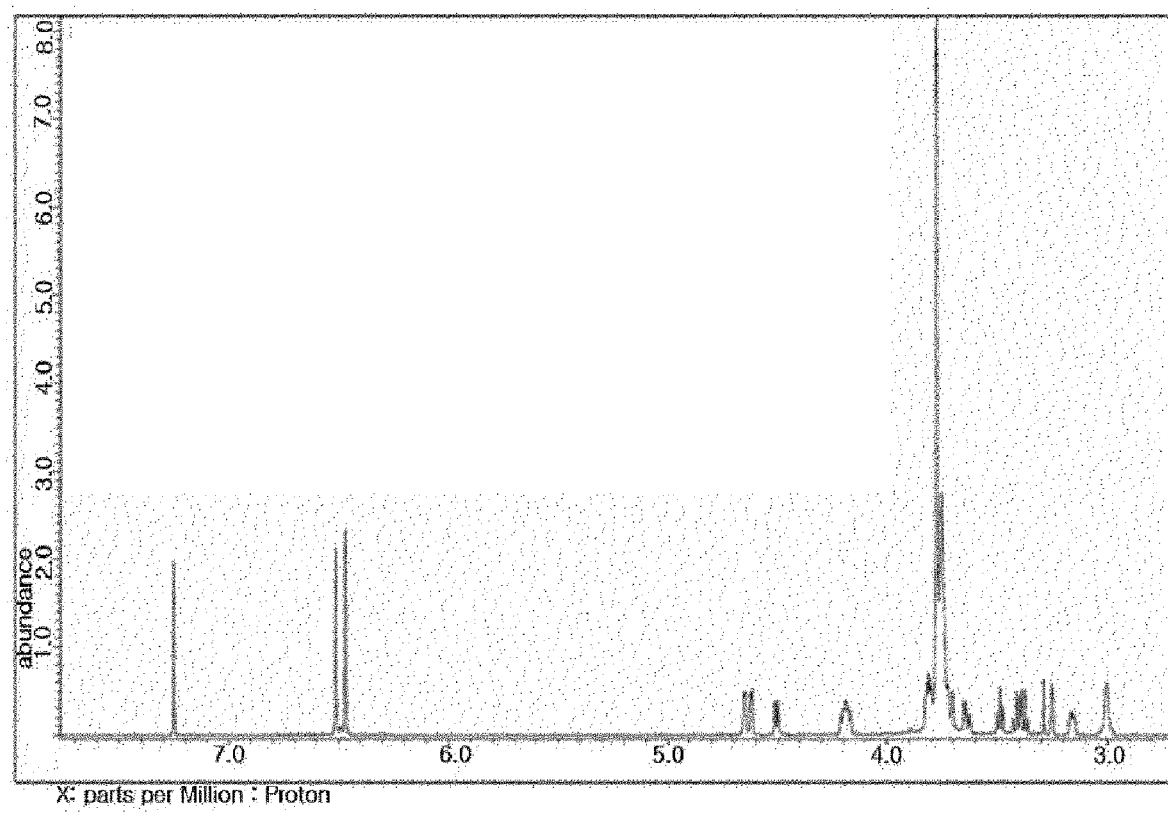
FIGS. 5a and 5b show NMR analysis results of the isolated compound S7-L3-3: (5a) $^1$H-NMR spectrum, (5b) $^{13}$C-NMR spectrum.
Figure 5B:
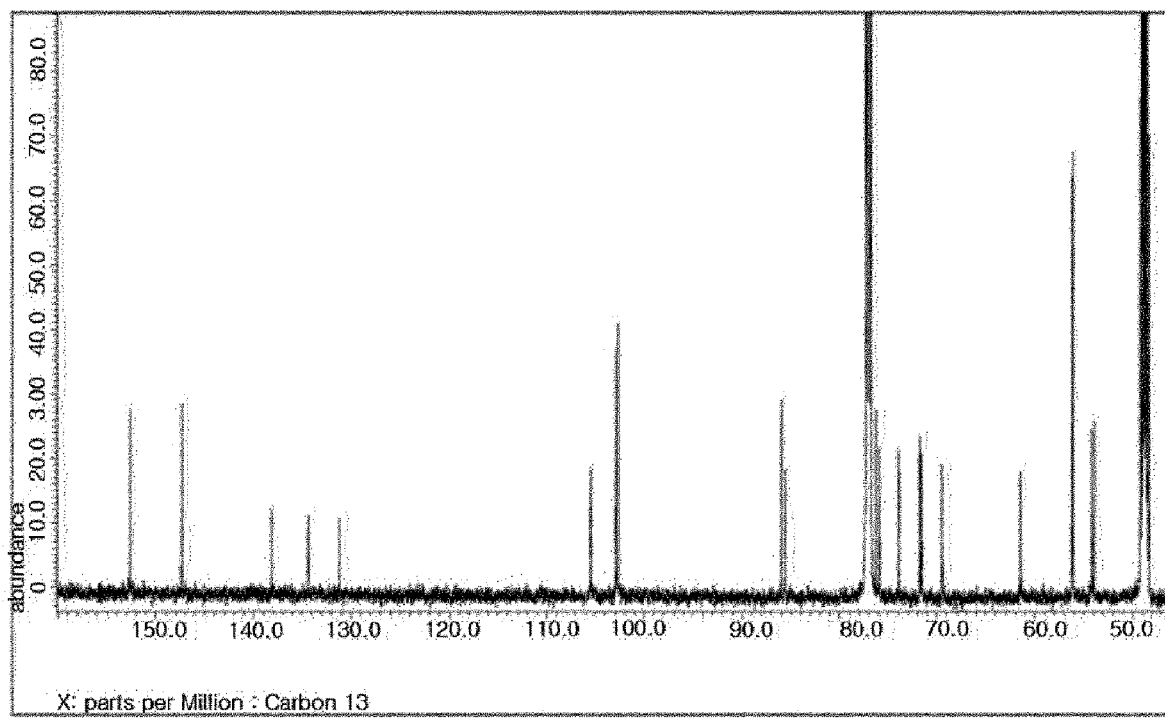

(1) Molecular formula: $C_{28}H_{36}O_{13}$
(2) Molecular weight: 580, ESI-MS: m/z 579.0 [M−H]$^+$, m/z 602.9 [M$^+$Na]$^+$ (FIG. 4)
(3) UV λmax: 210 nm, 238 sh, 272 nm
(4) Appearance: white powder
(5) Solubility: soluble in methanol, ethanol, ethyl acetate, ethyl acetate, chloroform, or pyridine
(6) $^1$H and $^{13}$C-NMR: $^1$H-NMR (CDCl$_3$, 600 MHz): d 6.47 (2H, s, H-2 and H-6), 4.62 (1H, d, J 4.6 Hz, H-7), 3.00 (1H, m, H-8), 3.81 (1H, m, H-9a), 4.19 (1H, m, H-9b), 6.51 (2H, 1H, H-2' and H-6'), 4.65 (1H, H-7'), 4.50 (1H. H-1"), 3.49 (1H, H-2"), 3.37 (1H, H-3"), 3.41 (1H, H-4"), 3.16 (1H. H-5"), 3.71 (1H, H-6"a), 3.64 (1H, H-6"b), 3.77 (6H, s, 2-OCH3), 3.78 (6H, s, 2-OCH3) (FIG. 5A); $^{13}$C-NMR (CDCl$_3$, 150 MHz): d131.2 (C-1), 102.3 (C-2), 147.3 (C-3), 134.4 (C-4), 147.3 (C-5), 102.7 (C-6), 86.0 (C-7), 53.9 (C-8), 71.6 (C-9), 56.1 (2X—OCH3), 56.2 (2Y—OCH3), 138.2 (C-1'), 102.9 (C-2'), 152.6 (C-3'), 134.4 (C-4'), 152.6 (C-5'), 102.9 (C-6'), 85.6 (C-7'), 54.2 (C-8'), 71.7 (C-9'), 105.4 (C-1"), 73.9 (C-2"), 75.9 (C-3"), 69.5 (C-4"), 76.2 (C-5"), 61.5 (C-6") (FIG. 5B)
(7) Chemical formula:

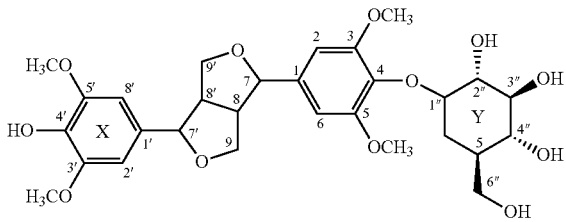

Example 6: Neuroglia Protective Effect of Desalted Salicornia europaea Extract (PM-EE)

Figure 8A:
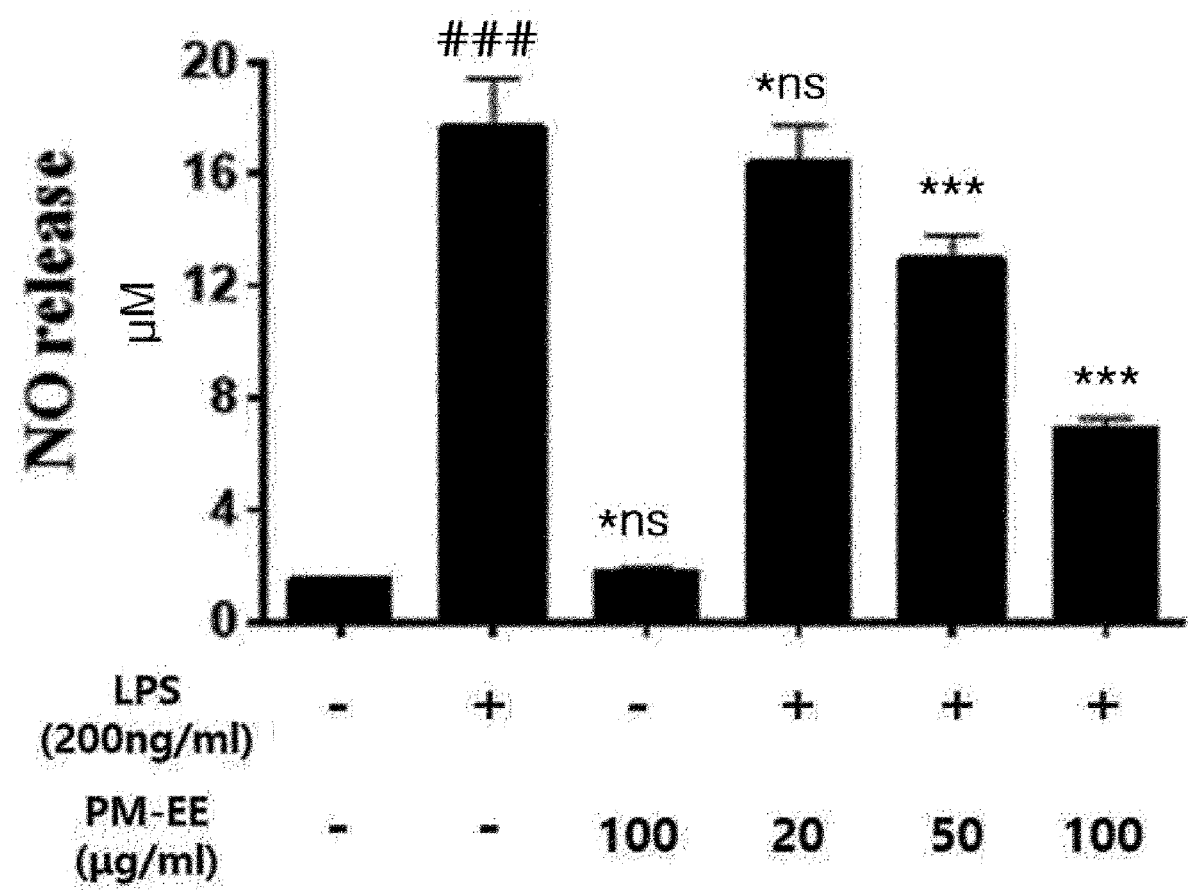
FIGS. 8a and 8b show neuroglial inflammation inhibitory effects of a desalted *Salicornia* spp. extract (PM-EE): (8a) LPS-induced nitrogen monoxide (NO) production inhibitory effect of PM-EE; and (8b) neuroinflammation factor protein (iNOS and COX-2) expression inhibitory effects of PM-EE.
Figure 8B:
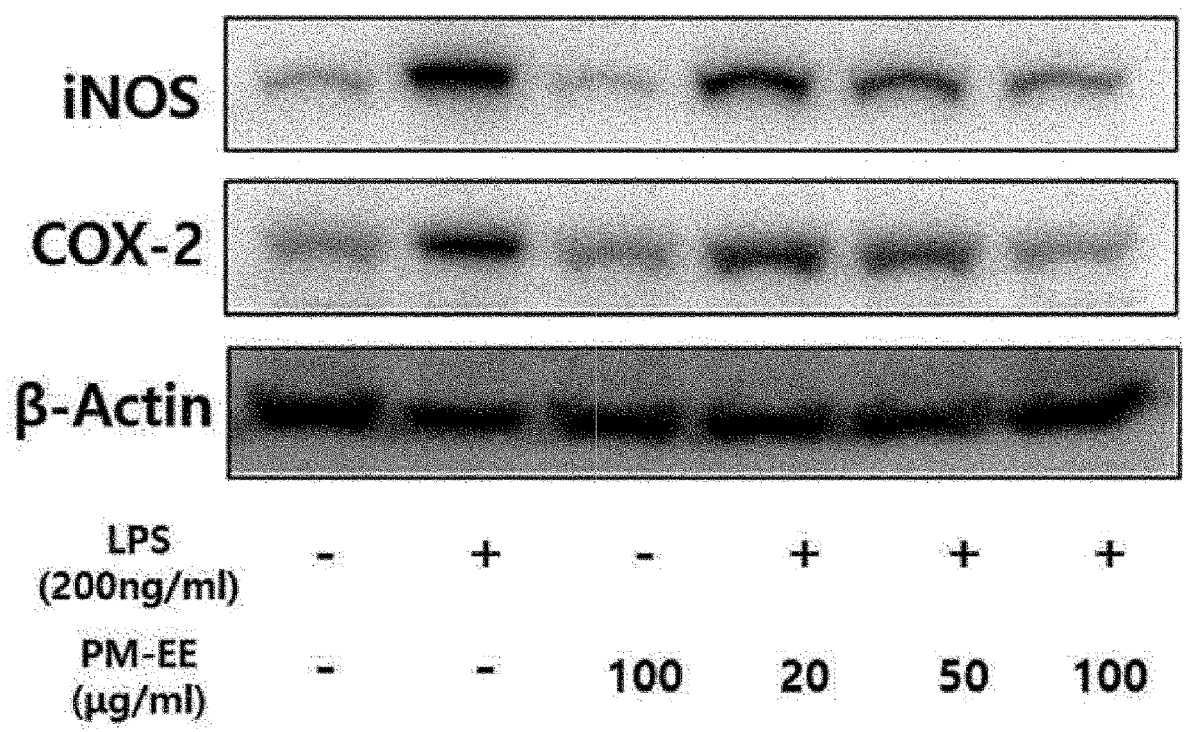

Test Example1. Confirmation of Neuroinflammation Factor Protein Expression Inhibitory Effect of PM-EE In order to investigate the effects of LPS (200 ng/ml), which is a neuroinflammation inducing substance, and a desalted Salicornia europaea extract (PM-EE, 0-100 μg/mL), which is a test sample, on neuroglia in BV2 microglia, which are LPS-stimulated neuroglia, the cytotoxicity test was conducted through MMT assay. As a result, it was verified that cell viability was not significantly changed in all the test material concentrations of LPS and PM-EE alone or together compared with control groups. Therefore, in order to analyze the neuroinflammation inhibitory ability of PM-EE at concentrations (20, 50, 100 μg/mL) without cytotoxicity, as for whether the nitric oxide (NO) produced in LPS (neuroinflammation inducing factor, 200 ng/ml)-stimulated mouse BV-2 microglia was inhibited by PM-EE treatment, the content of intracellular LPS-induced nitric oxide (NO) was measured through NO assay using Griess reagent. As can be seen in the results of FIG. 8a, the content of LPS-induced amplified intracellular nitric oxide (NO) was increased compared with a control group by about nine times. However, as a result of treatment with PM-EE at different concentrations (20, 50, and 100 μg/mL), the amount of nitric oxide (NO) was remarkably reduced dose-dependently (FIG. 8a). In addition, the expressions of inducible nitric oxide synthetase (iNOS) protein, which is an LPS-induced nitric oxide (NO) synthesis inducing enzyme, and cyclooxygenase type 2 (COX-2) protein known as a neuroinflammation factor, were examined by western blotting. As a result, it could be verified that PM-EE inhibited the expressions of iNOS and COX-2 dose-dependently in a protein stage (FIG. 8b).

Figure 9:
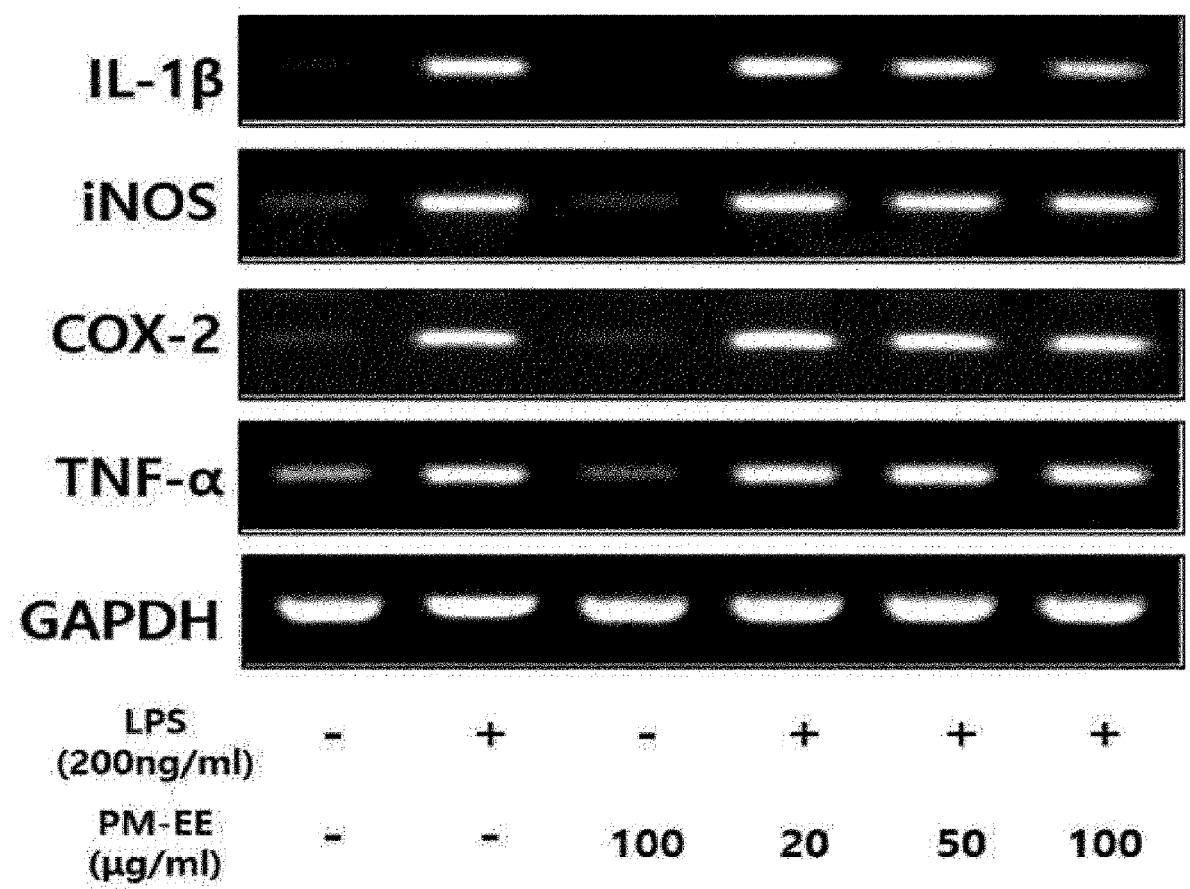
FIG. 9 shows results conforming neuroinflammation gene expression inhibitory effects of a desalted *Salicornia* spp. extract (PM-EE) through RT-PCR.

Test Example 2. Confirmation of Neuroinflammation Gene Expression Inhibitory Effect of PM-EE BV2 microglia as neuroglia were treated with LPS and the desalted Salicornia europaea extract (PM-EE) at different concentrations (0-100 μg/mL). After 1 hour, cells were stimulated by LPS, and after 3 hours, an RNA sample was isolated by an RNA extraction buffer. Thereafter, RT-PCR assay was conducted through RNA purification procedure. Table 4 below shows primers used in RT-PCR of the present test (SEQ ID NO: 1 to SEQ ID NO: 12). RNA isolated from BV2 microglia was subjected to denaturation at 95° C. for 30 minutes, 45 times of chain reactions in conditions of 95° C. for 5 seconds and 60° C. for 20 seconds, and annealing to 95° C. at 0.2° C./15 sec, using the primers in Table 4, and then the reaction was stopped. Last, separation by bp size was conducted through agarose gel electrophoresis. Then, bands were checked under UV, and fluorescence was imaged by a camera. As shown in the results in FIG. 9, the expressions of neuroinflammation-related genes (IL-1β, iNOS, COX-2, and TNF-α) were not or slightly observed in a control group treated without LPS. However, it could be verified that the mRNA expression levels of these genes were significantly increased in test groups treated with LPS. It could also be verified that the expression pattern was reduced dose-dependently at the time of the treatment with the desalted Salicornia europaea extract (PM-EE). It was especially verified that LPS-induced amplified neuroinflammation-related genes ((IL-1β, iNOS, COX-2, and TNF-α) at a high concentration (100 μg/mL) was restored to almost the same level as that of a control group before LPS induction. These results suggest that the desalted Salicornia europaea extract (PM-EE) can strongly inhibit neuroinflammation from mRNA gene stages as well as the neuroinflammation factor protein expression, in BV2 microglia as neuroglia. These results verified that PM-EE can improve brain cognitive ability by suppressing neuroinflammation to prevent brain impairment.

TABLE 4

| Gene | | Sequence (5'→3') |
|---|---|---|
| iNOS | Forward | TGAAGAAAACCCCTTGTGCT (SEQ ID NO: 1) |
| iNOS | Reverse | TTCTGTGCTGTCCCAGTGAG (SEQ ID NO: 2) |

TABLE 4-continued

| Gene | | Sequence (5'→3') |
|---|---|---|
| COX2 | Forward | CAAGACAGATCATAAGCGAGGA (SEQ ID NO: 3) |
| COX2 | Reverse | GGCGCAGTTTATGTTGTCTGT (SEQ ID NO: 4) |
| TNF-α | Forward | CCACCACGCTCTTCTGTCTAC (SEQ ID NO: 5) |
| TNF-α | Reverse | AGGGTCTGGGCCATAGAACT (SEQ ID NO: 6) |
| IL-1 β | Forward | TGTGAAATGCCACCTTTTGA (SEQ ID NO: 7) |
| IL-1 β | Reverse | GGTCAAAGGTTTGGAAGCAG (SEQ ID NO: 8) |
| IL-6 | Forward | TGATGCACTTGCAGAAAACA (SEQ ID NO: 9) |
| IL-6 | Reverse | ACCAGAGGAAATTTTCAATAGGC (SEQ ID NO: 10) |
| GAPDH | Forward | AAGGGCTCATGACCACAGTC (SEQ ID NO: 11) |
| GAPDH | Reverse | TTCAGCTCTGGGATGACCTT (SEQ ID NO: 12) |

Figure 10A:
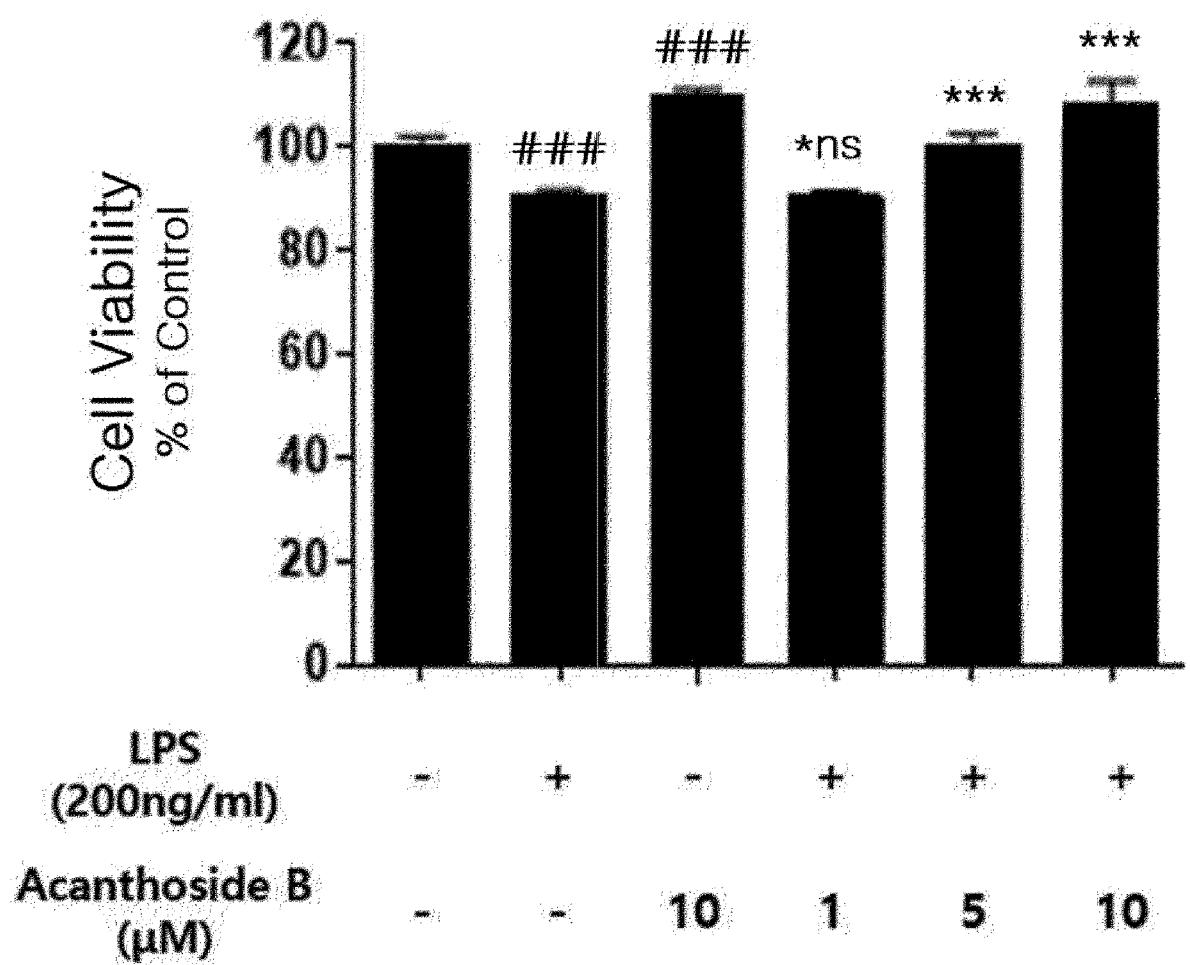
FIGS. 10a to 10c show neuroglial inflammation inhibitory effects of acanthoside B isolated from a desalted *Salicornia* spp. extract (PM-EE): (10a) Cytotoxicity test of acanthoside B through MTT assay; (10b) LPS-induced nitrogen monoxide (NO) production inhibitory effect of acanthoside B; and (10c) neuroinflammation factor protein (iNOS and COX-2) expression inhibitory effects of acanthoside B.
Figure 10B:
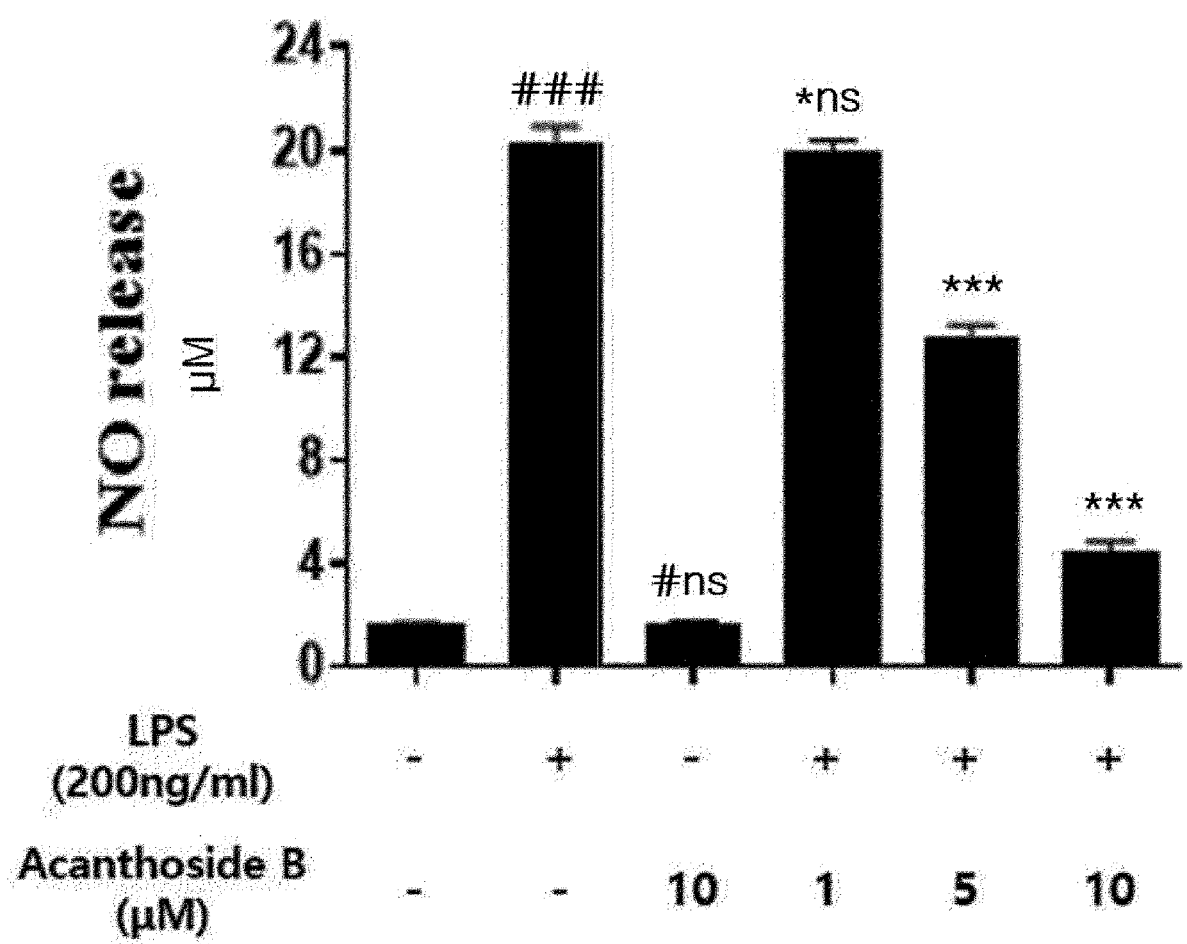
Figure 10C:
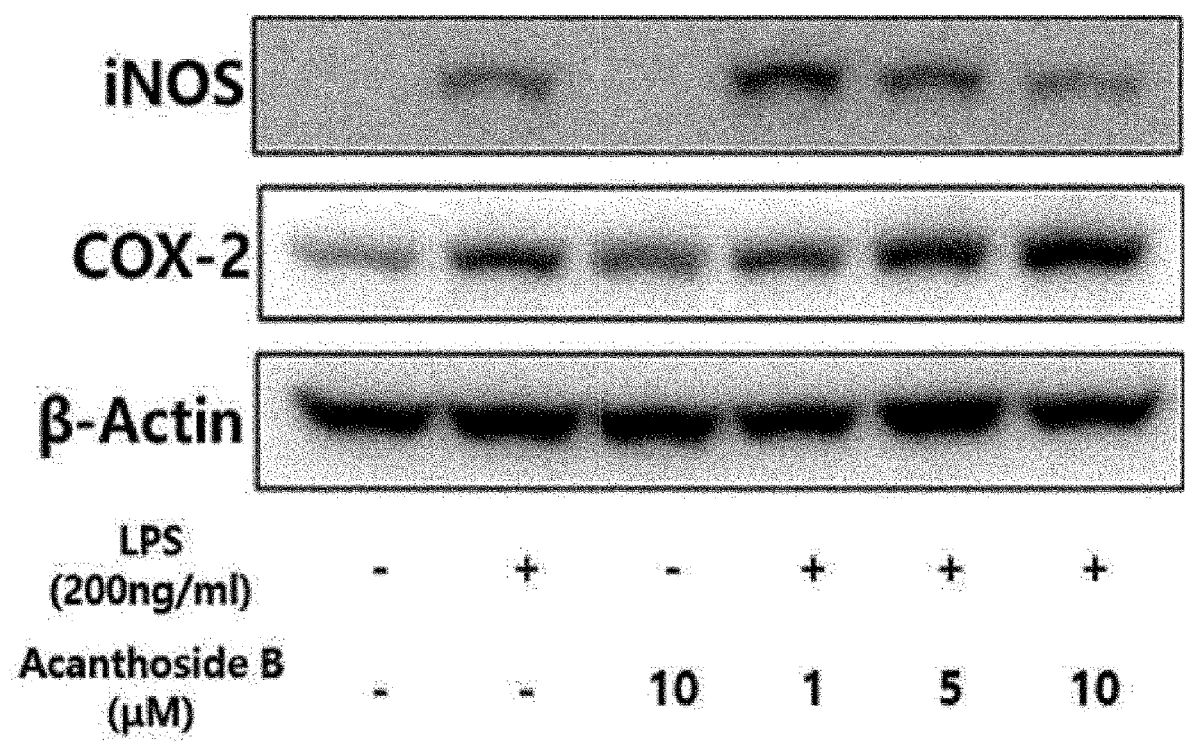

Example 7: Neuroglia Protective Effect of Active Ingredient Acanthoside B Isolated from PM-EE Test Example 1: Confirmation of Neuroinflammation Factor Protein Expression Inhibitory Effect of Acanthoside B A test was conducted to investigate effects of the neuroinflammation inducing substance LPS (200 mg/mL) and the active ingredient acanthoside B of PM-EE on brain glia cells in LPS-stimulated brain glia cells BV2 microglia. The cells were treated with each material at different concentrations (1, 5, 10 µg/mL), and a cytotoxicity test was conducted through MTT analysis. As a result, it was verified that the cell viability was not significantly changed in all the test material concentration groups treated with LPS and acanthoside B alone or together compared with a control group (FIG. 10a). Therefore, in order to analyze the neuroinflammation inhibitory ability of acanthoside B at concentrations (1, 5, 100 µg/mL) without cytotoxicity, as for whether the nitric oxide (NO) produced in LPS (200 ng/ml)-stimulated mouse BV-2 microglia was inhibited by acanthoside B, the content of intracellular LPS-induced nitric oxide (NO) was measured through NO assay using Griess reagent. It could be verified from the results of FIG. 10b that LPS-induced amplified intracellular nitric oxide (NO) was remarkably decreased dependently on the treatment concentration of acanthoside B. In addition, it was verified through western blotting that the expressions of iNOS, which is an LPS-induced nitric oxide (NO) synthesis inducing enzyme, and COX-2, which is an neuroinflammation factor, were remarkably inhibited (FIG. 10c). Therefore, it was verified that acanthoside B, which is a neuroinflammation inhibiting active ingredient in PM-EE, inhibited the expressions of iNOS and COX-2 proteins even at a remarkably low concentration compared with PM-EE.

Figure 11:
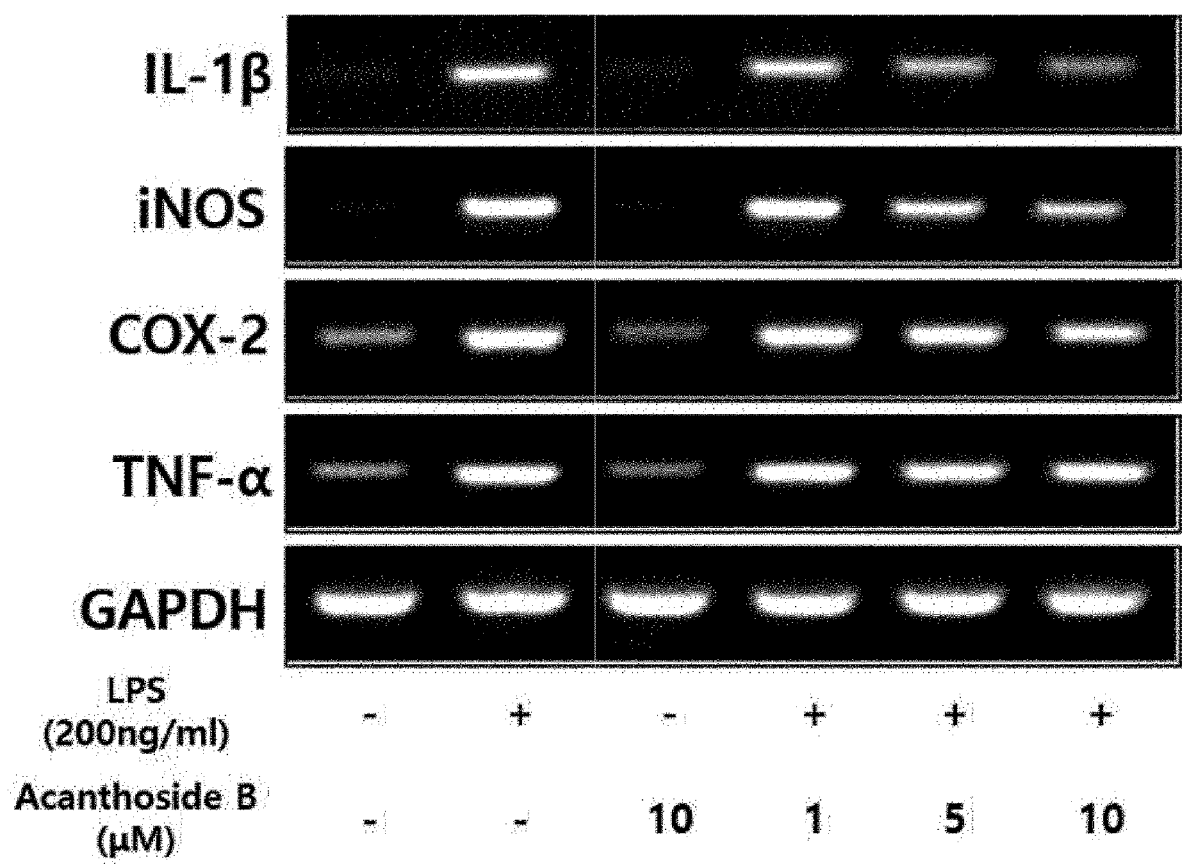
FIG. 11 shows results conforming neuroinflammation gene expression inhibitory effects of acanthoside B isolated from a desalted *Salicornia* spp. extract (PM-EE) through RT-PCR.

Test Example 2. Confirmation of Neuroinflammation Factor Gene Expression Inhibitory Effect of Acanthioside B A test was conducted to investigate an effect of acanthoside B on neuroinflammation factor gene expression. The BV2 microglia as neuroglia were treated with LPS and acanthoside B at different concentrations (1, 5, 10 µg/mL), and after 1 hour, cells were stimulated by LPS. After 3 hours, RNA sample was separated by RNA extraction buffer to synthesize cDNA, and RT-PCR was conducted by the same method as in example 6 using the primers in Table 4. As shown in the results in FIG. 11, the expressions of neuroinflammation-related genes (IL-1β, iNOS, COX-2, and TNF-α) were not or slightly observed in a control group treated without LPS. However, it could be verified that the mRNA expression levels of these genes were significantly increased in test groups treated with LPS. It could also be verified that the expression pattern was reduced dose-dependently at the time of the treatment with acanthoside B. It was especially verified that LPS-induced amplified neuroinflammation-related genes (IL-1β, iNOS, COX-2, and TNF-α) at a high concentration (10 µg/mL) was restored to almost the same level as that of a control group before LPS induction. Therefore, it could be verified that acanthoside B as an AChE inhibiting active ingredient isolated from PM-EE acts on neuroinflammation from mRNA gene stages as well as the neuroinflammation factor protein expression, thereby inhibiting neuroinflammation to prevent brain impairment, thus improving brain cognitive ability.

Figure 12A:
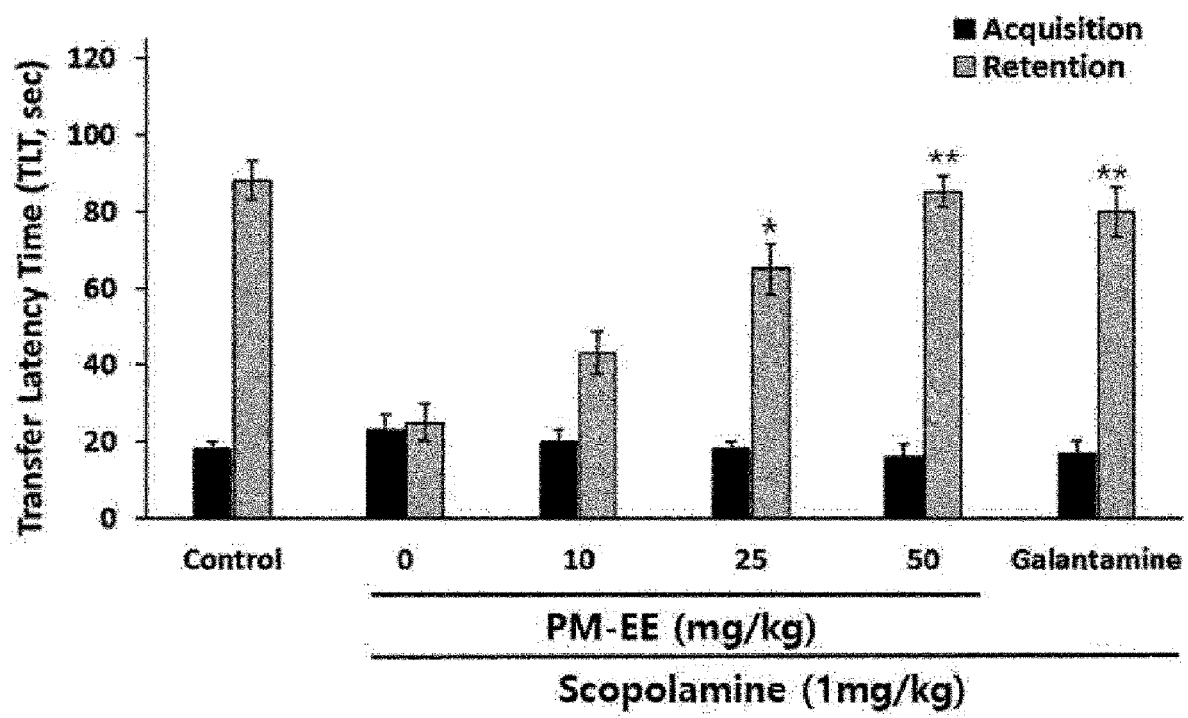
FIGS. 12a and 12b show passive avoidance test results at the time of administration of a desalted *Salicornia* spp. extract (PM-EE) and acanthoside B in forgetfulness animal models using scopolamine: (12a) PM-EE treatment effect; and (12b) acanthoside B treatment effect.
Figure 12B:
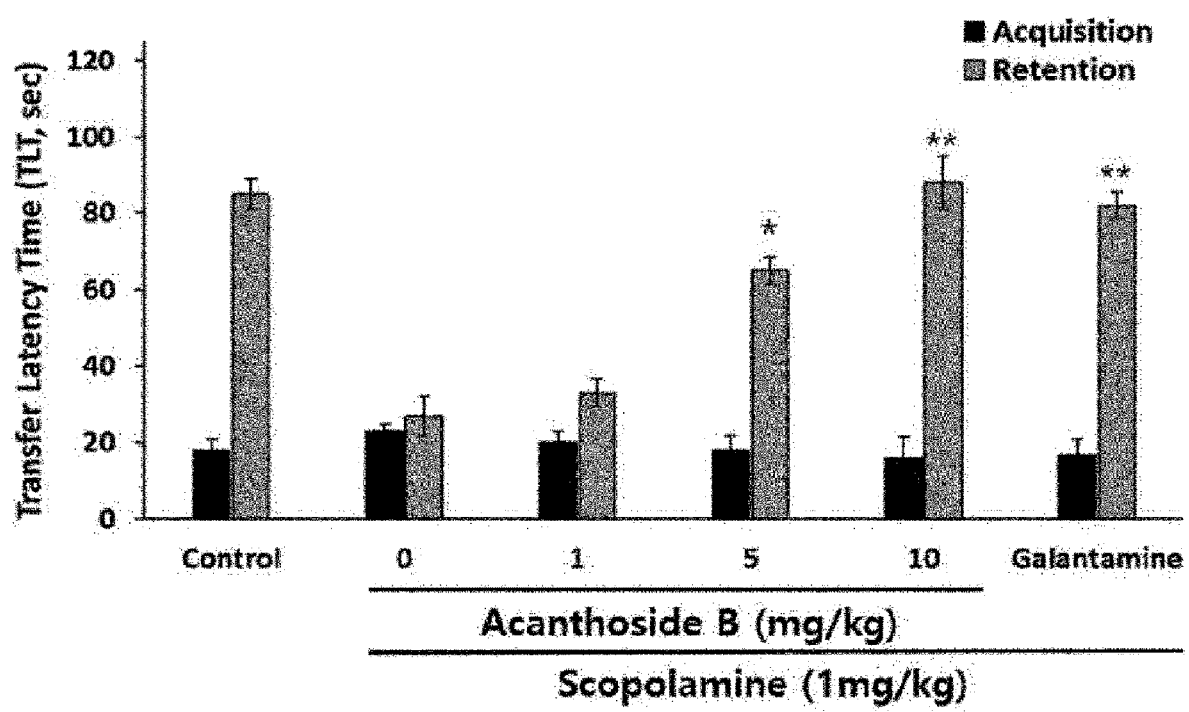

Example 8: Confirmation of Improvement of Memory and Cognitive Ability of Desalted *Salicornia europaea* Extract (PM-EE) and Active Ingredient (Acanthoside B) Thereof in Cognitive Ability Impairment Animal Models Test Example 1. Analysis of Cognitive Ability and Memory Improvement Efficacy of PM-EE and Acanthoside B in In-Vivo Cognitive Ability Impairment Models A test was conducted to investigate the improvement efficacy of cognitive ability and memory of the desalted *Salicornia europaea* extract (PM-EE) obtained in example 4-1 above and acanthoside B as an AChE inhibitory and neuroinflammation inhibiting substance isolated from PM-EE in examples 4-2 and 4-3. The learning ability effect was measured through a passive avoidance test in forgetfulness animal models using scopolamine. Mice were placed in the bright section with shining light and allowed to go over for 20 seconds. Subsequently, the guillotine door was opened and the mouse was allowed to enter into the dark section. Here, mice that did not enter the dark section within 60 seconds after the guillotine door was opened were excluded from the test. The time from when the guillotine door was opened to when the mouse entered the dark section was measured. Once the mouse entered the dark section, the guillotine door was closed, and an electric shock of 0.25 mA flows through a grid bottom for 3 seconds, and the mouse remembered this electrical action. The present test was conducted 24 hours after the learning test. For the test, 10 SD rates (240-260 g) per group were treated with PM-EE and acanthoside B at different concentrations, and at 30 minutes after the final administration of a test sample, scopolamine (Sigma-Aldrich, Co. USA) dissolved in distilled water was intraperitoneally administered at a dose of 1 mg/kg. At 30 minutes after the administration of scopolamine, the mouse was allowed to go over for 10 seconds, and then the time taken for four feet of the mouse to enter the dark section after the opening of the guillotine door (transfer latency time, TLT: retention time) was measured up to 150 seconds. Here, the longer the time taken, the better the cognitive ability and memory in passive avoidance. In addition, separately from PM-EE, which is the desalted *Salicornia europaea* extract sample, and acanthoside B, mg/kg of the dementia drug galantamine (Sigma-Aldrich, Co. USA) as a positive control group was administered. As a result of recording the transfer latency time (TLT) through a computer, the retention time in the groups administered with only scopolamine was significantly reduced in all the experiments, confirming that memory and cognitive ability decline models were fabricated. It could also be verified that in cognitive ability and memory impairment mouse models, the impaired cognitive ability was improved by the treatment with PM-EE (FIG. 12a) and acanthoside B (FIG. 12b), confirming that TLT was significantly increased. All of the above effects are considered to bed dose-dependent, and especially the administration of PM-EE and acanthoside B at high concentrations showed more superior cognitive ability and memory improvement effects compared with the dementia drug, galantamine.

Test Example 2. Analysis of Cognitive Ability and Memory Improvement Efficacy in Y-Maze Test A test was conducted to investigate the improvement efficacy of cognitive ability and memory of the desalted *Salicornia europaea* extract (PM-EE) obtained in example 4-1 above and acanthoside B as an AChE inhibitory and neuroinflammation inhibiting substance isolated from PM-EE in examples 4-2 and 4-3. The Y-maze test was conducted in forgetfulness animal models using scopolamine. In the present test, PM-EE and acanthoside B were dissolved in 10% Tween 80, and then the mixture was orally administered at different concentrations (PM-EE and acanthoside B). In addition, 10 mg/kg of the dementia drug galantamine (Sigma-Aldrich, Co. USA) as a positive control group was administered. For the Y-maze test, a test animal was carefully placed in a test apparatus composed of three arms (A, B, C) of a black polyvinyl plastic, each of the arms being 50 cm in length, 10 cm in width, and 20 cm in height, and the folding angle of the three arms being 120 degrees, and the test animal was allowed to freely move for 8 minutes, and then the number of arm entries was recorded. If the test animal sequentially entered the three different arms, 1 point (actual alternation) was given. The alternation behavior was calculated by the following formula.

Alternation behavior=(actual alternation)/(maximum alternation)×100 (maximum alternation: the total number of arm entries−2)

Figure 13A:
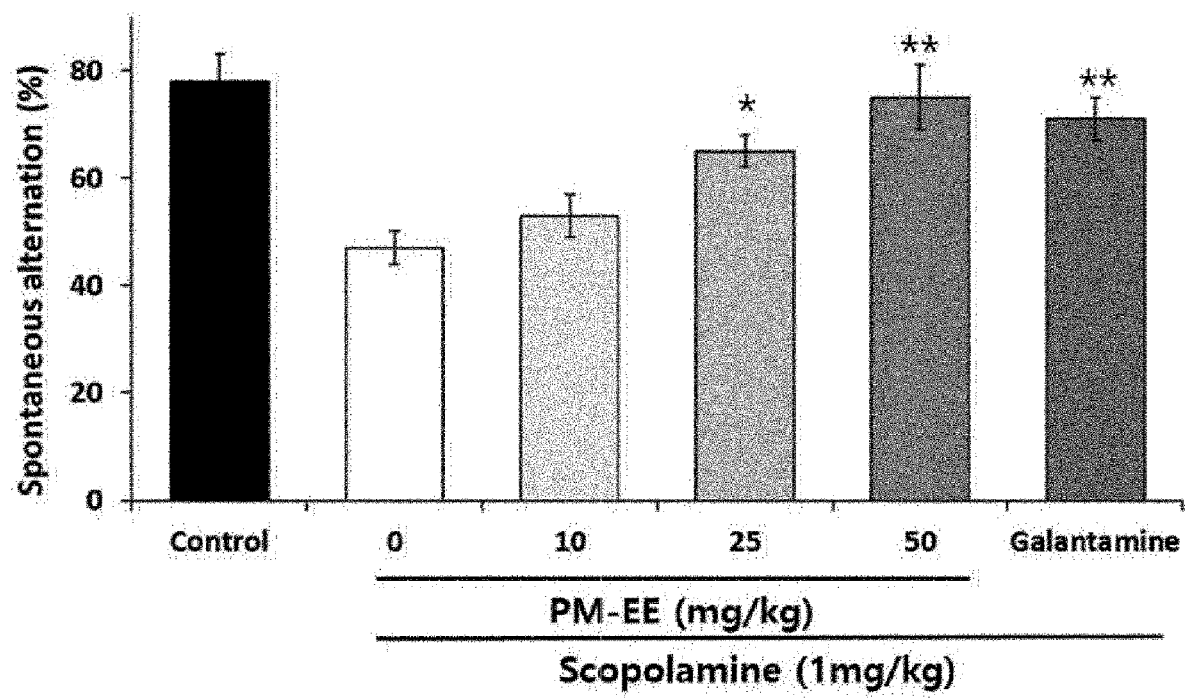
FIGS. 13a and 13b show Y-maze test results at the time of administration of a desalted *Salicornia* spp. extract (PM-EE) and acanthoside B in forgetfulness animal models using scopolamine: (13a) PM-EE treatment effect; and (13b) acanthoside B treatment effect.
Figure 13B:
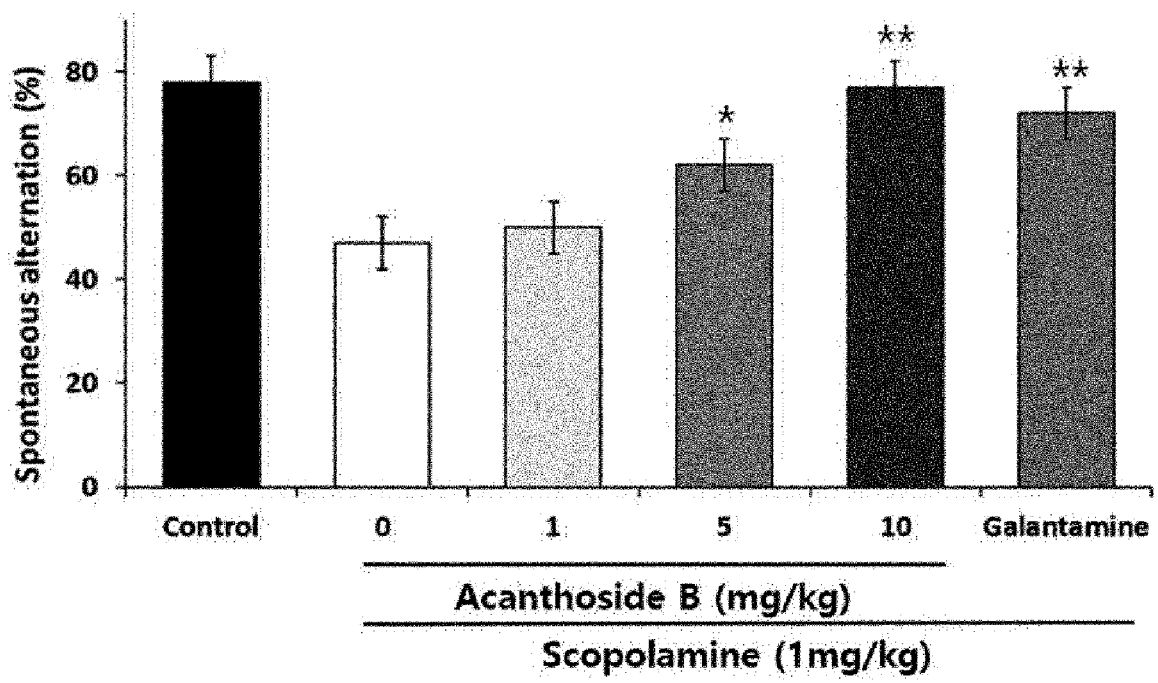

As test results, the behavior of a normal animal, that is, a control group, scored 50 points, but reduced to 45.5 points by the administration of scopolamine, showing declines in cognitive ability and memory. It could also be verified that the alternation behavior, that is, spatial cognitive ability was again restored dose-dependently due to the administration of PM-EE and acanthoside B. Therefore, it was verified that PM-EE (FIG. 13a) and acanthoside B (FIG. 13b) showed superior cognitive ability and memory improvement effects to galantamine as a dementia medicine.

Example 9: Single Doing Toxicity Test

A single dosing toxicity test on a desalted *Salicornia europaea* extract (PM-EE) was conducted using mice. As a result of the single dosing toxicity test, no death cases were observed when PM-EE was administered at 2 g/kg, which is an available dose defined by ICH, for 2 weeks. In addition, no significant abnormality was observed in weight gain, feed intake, and the like. Therefore, it could be seen that the desalted *Salicornia europaea* extract (PM-EE) containing acanthoside of the present invention can be developed as a safe drug for prevention and treatment of dementia, a health functional food raw material and a feed.

---

The invention claimed is:

1. A method for isolating acanthoside B, the method comprising the steps of:
   (a) obtaining (i) a polar solvent extract or (ii) an enzymatic hydrolysis extract from *Salicornia* spp.;
   (b) adding an acidic solution to the resultant product in step (a), followed by stirring and standing, to eliminate precipitates;
   (c) adding a basic solution to the resultant product in step (b) and then adding a non-polar organic solvent thereto to obtain an alkaloid fraction; and
   (d) purifying the alkaloid fraction in step (c) to obtain acanthoside B as a single substance.

2. The method of claim 1, wherein the non-polar organic solvent in step (c) is chloroform, hexane, ethyl acetate, methyl acetate, fluoroalkane, pentane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, dichloromethane, 1,2-dichloroethane, aniline, diethyl amine, ether, carbon tetrachloride or tetrahydrofuran (THF).

3. The method of claim 1, wherein in step (d) purifying the alkaloid fraction using a high-performance liquid chromatography.

* * * * *